(12) United States Patent
Krubsack et al.

(10) Patent No.: US 10,856,756 B2
(45) Date of Patent: Dec. 8, 2020

(54) TIME-FREQUENCY ANALYSIS OF ELECTROCARDIOGRAMS

(71) Applicant: Heart Test Laboratories, Inc., Southlake, TX (US)

(72) Inventors: David Krubsack, Allen, TX (US); Aaron Peterson, Frisco, TX (US)

(73) Assignee: HEART TEST LABORATORIES, INC., Southlake, TX (US)

( * ) Notice: Subject to any disclaimer, the term of this patent is extended or adjusted under 35 U.S.C. 154(b) by 0 days.

(21) Appl. No.: 16/127,676

(22) Filed: Sep. 11, 2018

(65) Prior Publication Data

US 2019/0076044 A1 Mar. 14, 2019

Related U.S. Application Data

(60) Provisional application No. 62/556,907, filed on Sep. 11, 2017.

(51) Int. Cl.
| | | |
|---|---|---|
| *A61B 5/04* | (2006.01) |
| *A61B 5/0402* | (2006.01) |
| *A61B 5/00* | (2006.01) |
| *A61B 5/044* | (2006.01) |
| *A61B 5/0452* | (2006.01) |
| *A61B 5/0245* | (2006.01) |
| *A61B 5/0472* | (2006.01) |

(Continued)

(52) U.S. Cl.
CPC ........ *A61B 5/04014* (2013.01); *A61B 5/0245* (2013.01); *A61B 5/0402* (2013.01); *A61B 5/044* (2013.01); *A61B 5/0452* (2013.01); *A61B 5/0472* (2013.01); *A61B 5/726* (2013.01); *A61B 5/7257* (2013.01); *A61B 5/7275* (2013.01); *A61B 5/743* (2013.01); *A61B 5/7425* (2013.01); *A61B 5/04017* (2013.01); *A61B 5/0456* (2013.01); *A61B 5/0468* (2013.01)

(58) Field of Classification Search
None
See application file for complete search history.

(56) References Cited

U.S. PATENT DOCUMENTS 5,827,195 A * 10/1998 Lander ................ A61B 5/0452
600/509
2013/0165781 A1* 6/2013 Cardinale ............ A61B 5/044
600/440

(Continued)

FOREIGN PATENT DOCUMENTS

WO WO-2019051473 A1 3/2019

OTHER PUBLICATIONS

"International Application Serial No. PCT/US2018/050415, International Search Report dated Dec. 6, 2018", 4 pgs.

(Continued)

*Primary Examiner* — Ankit D Tejani
(74) *Attorney, Agent, or Firm* — Schwegman Lundberg & Woessner, P.A.

(57) ABSTRACT

Electrocardiograms can be analyzed in the time-frequency domain, following conversion into time-frequency maps, to determine characteristics or features of various waveforms, such as waveform morphology and/or the amplitude(s) and location(s) (in time and/or frequency) of one or more extrema of the waveform. Based on comparison of the extrema against thresholds and/or against each other, disease conditions may be determined.

24 Claims, 14 Drawing Sheets

(51) Int. Cl.
*A61B 5/0456* (2006.01)
*A61B 5/0468* (2006.01)

(56) References Cited

U.S. PATENT DOCUMENTS

| | | |
|---|---|---|
| 2013/0178755 A1 | 7/2013 | Waters |
| 2017/0086696 A1 | 3/2017 | Chen et al. |
| 2017/0196473 A1 | 7/2017 | Krubsack et al. |
| 2017/0224995 A1* | 8/2017 | Sanghera ............ A61N 1/36585 |
| 2017/0225001 A1* | 8/2017 | Zaidi .................... A61N 1/0484 |

OTHER PUBLICATIONS

"International Application Serial No. PCT/US2018/050415, Written Opinion dated Dec. 6, 2018", 8 pgs.
"International Application Serial No. PCT/US2018/050415, International Preliminary Report on Patentability dated Mar. 26, 2020", 10 pgs.

* cited by examiner

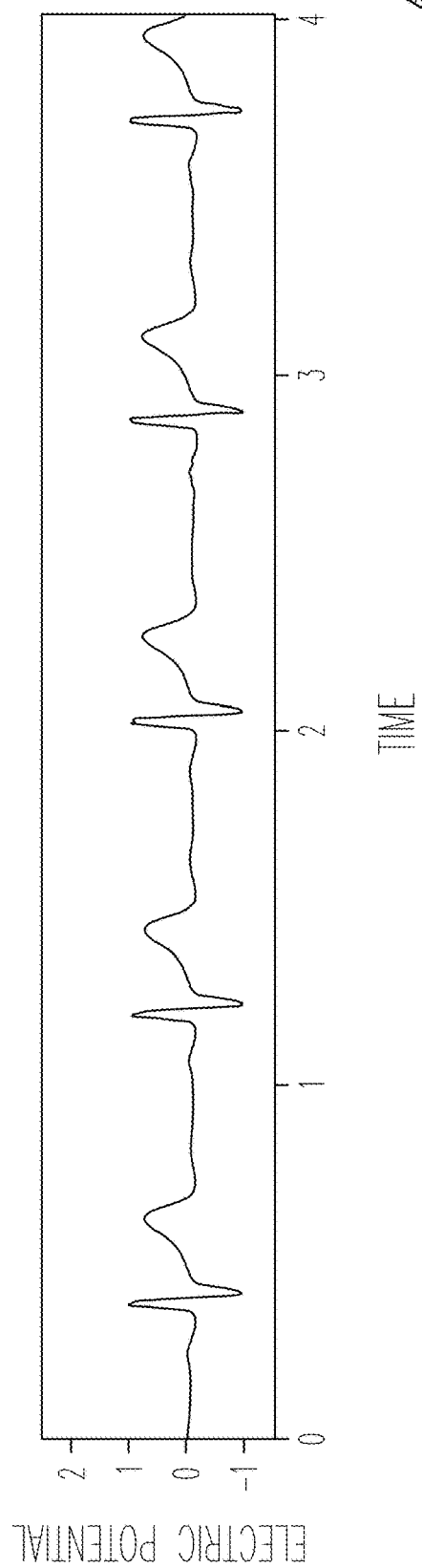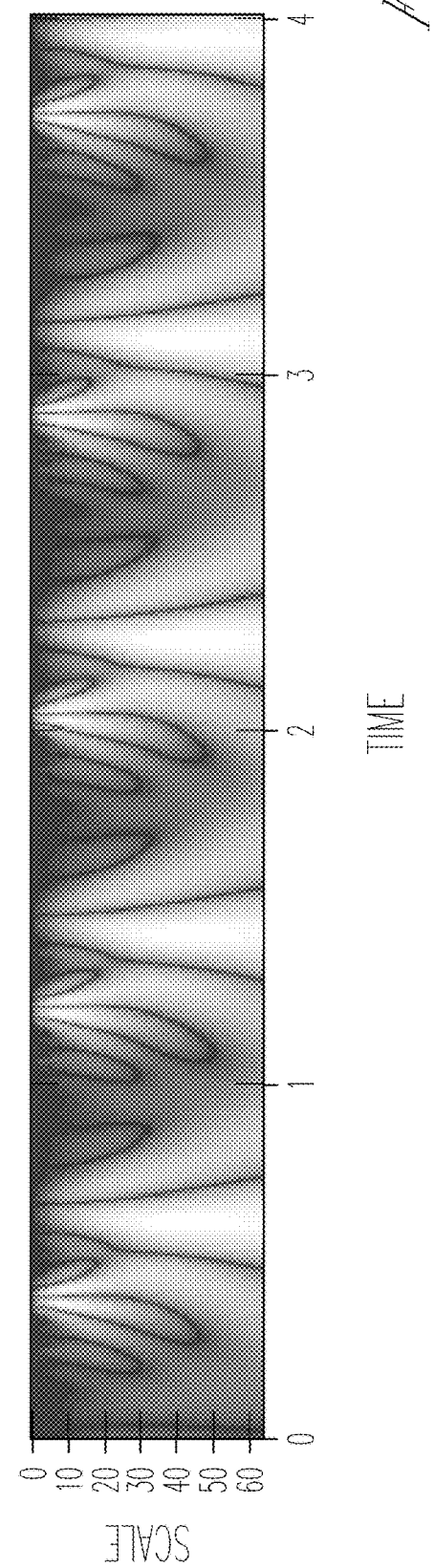

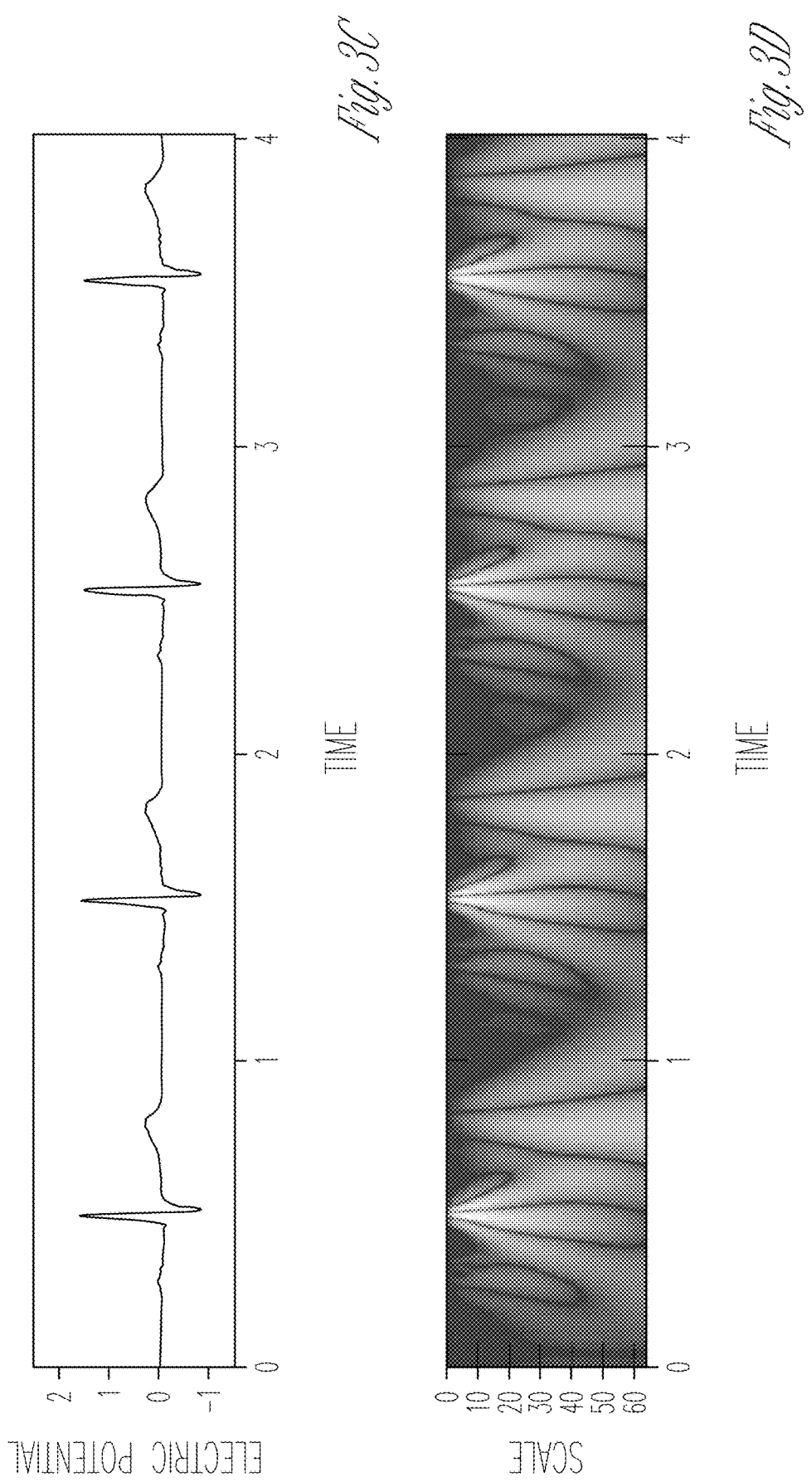

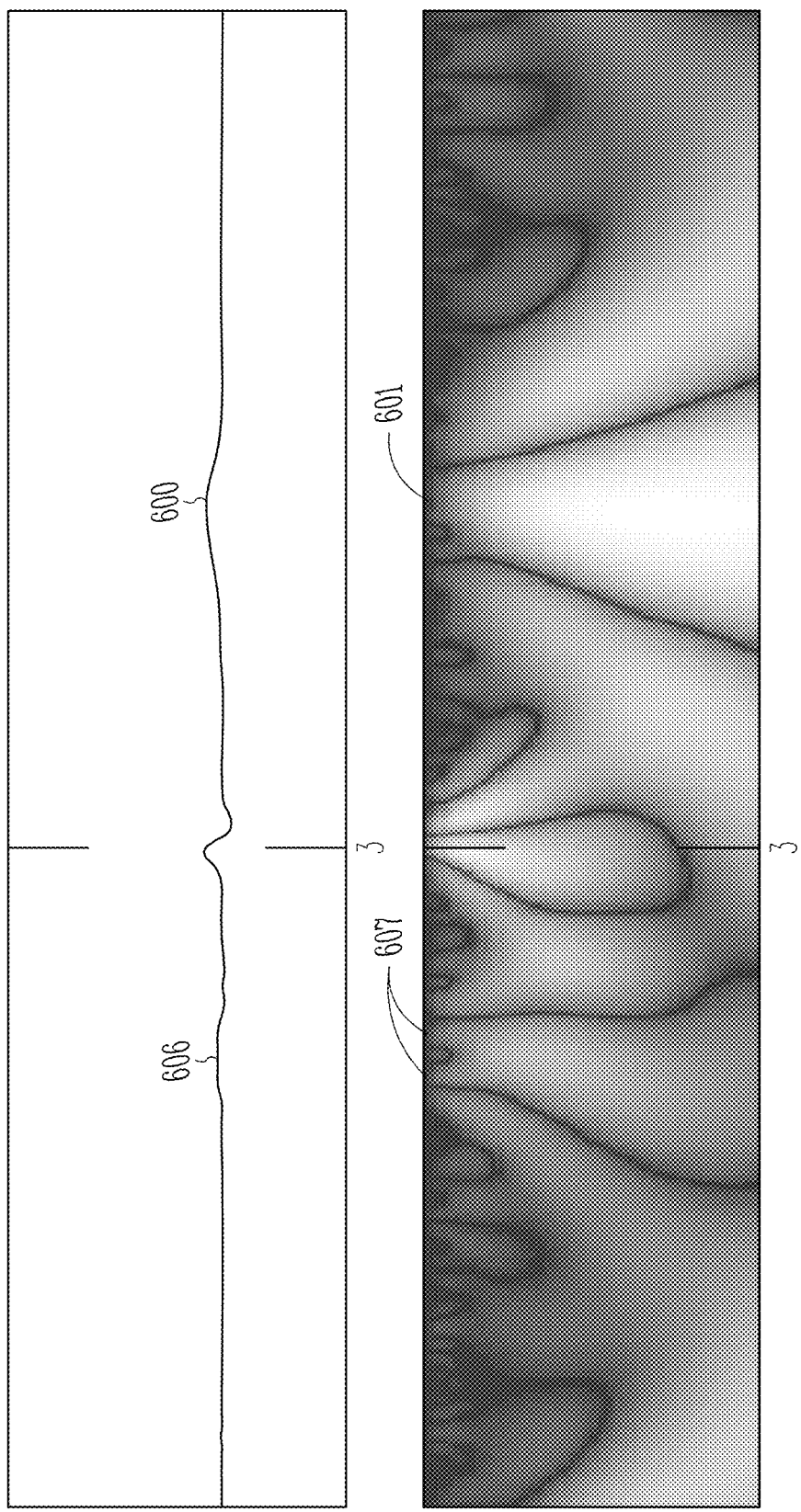

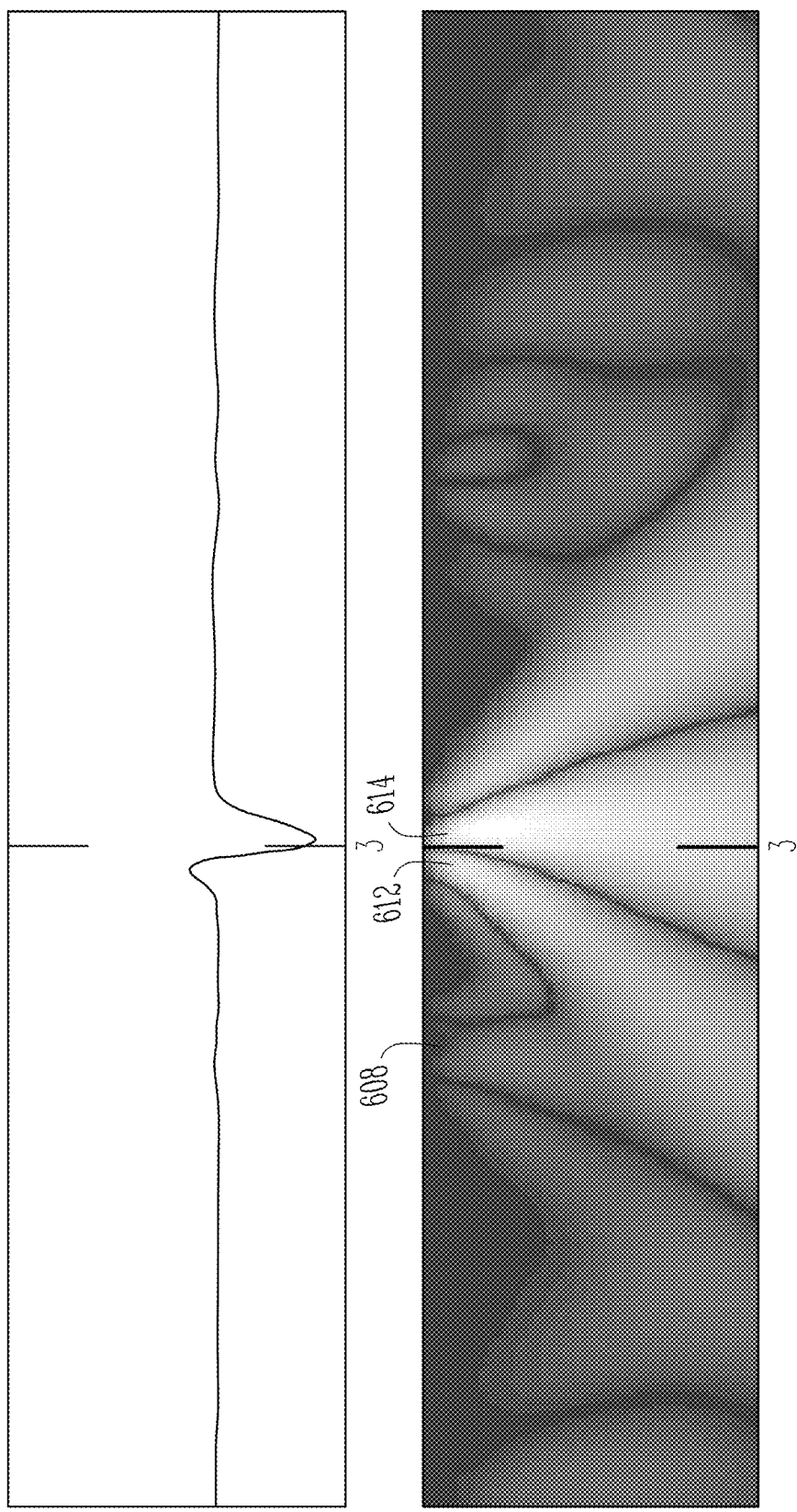

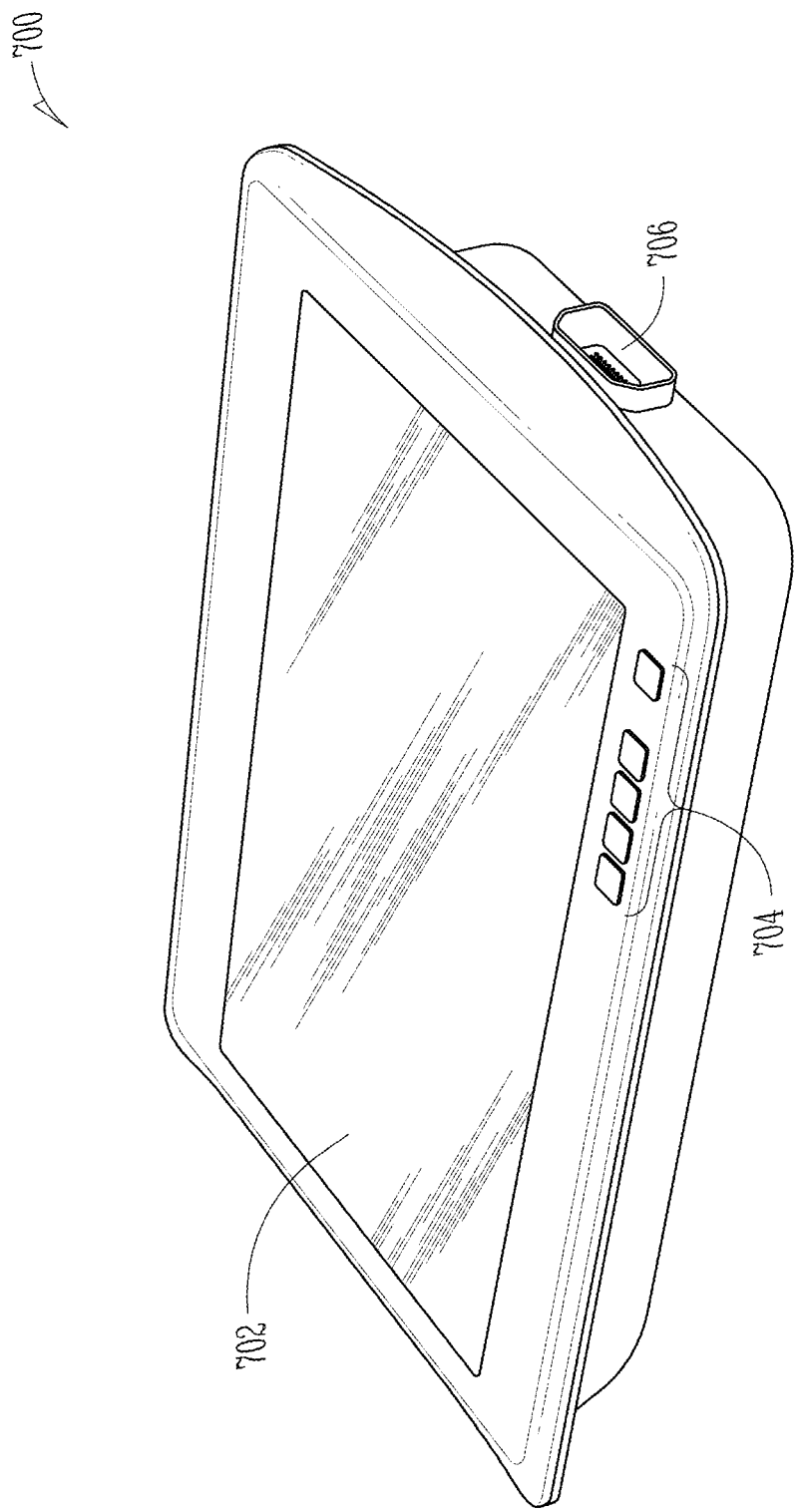

TIME-FREQUENCY ANALYSIS OF ELECTROCARDIOGRAMS

CROSS-REFERENCE TO RELATED APPLICATION

This application claims priority to and the benefit of U.S. Provisional Patent Application No. 62/556,907, filed on Sep. 11, 2017 and entitled "Time-Frequency Analysis of Electrocardiogram," which is hereby incorporated herein by reference in its entirety.

TECHNICAL FIELD

The present disclosure relates generally to cardiac diagnostics, specifically to systems, devices, and methods for electrocardiogram (ECG) analysis.

BACKGROUND

Heart testing for coronary heart disease, myocardial ischemia, and other abnormal heart conditions is routinely performed using ECGs, which represent electrical potentials reflecting the electrical activity of the heart measured via electrodes placed on the patient's skin. The heart's electrical system controls timing of the heartbeat by sending an electrical signal through the cells of the heart. The heart includes conducting cells for carrying the heart's electrical signal, and muscle cells that contract the chambers of the heart as triggered by the heart's electrical signal. The electrical signal starts in a group of cells at the top of the heart called the sinoatrial (SA) node. The signal then travels down through the heart, conducting cell to conducting cell, triggering first the two atria and then the two ventricles. Simplified, each heartbeat occurs by the SA node sending out an electrical impulse. The impulse travels through the upper heart chambers, called "atria," electrically depolarizing the atria and causing them to contract. The atrioventricular (AV) node of the heart, located on the interatrial septum close to the tricuspid valve, sends an impulse into the lower chambers of the heart, called "ventricles," via the His-Purkinje system, causing depolarization and contraction of the ventricles. Following the subsequent repolarization of the ventricles, the SA node sends another signal to the atria to contract, restarting the cycle. This pattern, and variations therein as may result, e.g., from an abnormality in heart function, can, in principle, be captured in an ECG, allowing medically trained personnel to draw inferences about the heart's condition from the ECG. However, subtleties and complexities in the signals, variations between signals for different leads (corresponding to different electrodes or combinations of electrodes), and/or low signal levels for features of interest can render the reading and interpretation of the ECG difficult, and hinder an unambiguous and accurate diagnosis. For example, developing abnormalities are often not immediately visible in an ECG as analyzed in a conventional manner, which causes many patients to be misdiagnosed as healthy.

SUMMARY

Described herein, in various embodiments, are systems, devices, and methods for enhancing the analysis of ECGs through advanced signal processing in the time-frequency domain, e.g., to resolve ambiguities in identifying waveforms or other features within the signals and/or increase the accuracy and/or diagnostic relevance of qualitative characterizations of and/or quantitative measures derived for these features.

In accordance with various embodiments, ECGs—i.e., time-domain signals reflecting the electric potential of the heart throughout one or more cardiac cycles—are computationally converted, by a suitable time-frequency transform, into respective two-dimensional time-frequency maps. In a "time-frequency map," as the term is herein broadly understood, the signal value (corresponding, e.g., to a measured electric potential) is provided as a function of two independent variables: time, and a measure of the spectral components of the signal such as, e.g., frequency (in the narrower sense) or a scaling factor. For example, in some embodiments, short-time Fourier transform is used to convert the ECGs into spectrograms, where the signal value is a function of time and frequency. In other embodiments, the ECGs are converted by (continuous or discrete) wavelet transform into so-called scalograms, where the signal value is a function of time and a scaling factor. More generally, a filter bank may be used to transform the ECG into a time-frequency representation. For ease of reference, the dimension of the time-frequency map that corresponds to the frequency or scaling factor (or any other measure of the spectral components) is herein generally referred to as the frequency dimension or simply frequency.

The time-frequency maps, by themselves or in conjunction with the ECGs from which they are derived, may be displayed to a physician (or other clinical personnel) for interpretation, and/or analyzed automatically, e.g., to derive quantitative metrics of heart condition and function therefrom. By spreading out the spectral components of the measured ECG signals, the time-frequency maps can visualize information not or not easily and unambiguously discernible from the ECGs themselves, which can improve the accuracy of diagnostic determinations and may even help detect conditions traditionally not diagnosed based on ECGs (such as, e.g., myocardial ischemia).

In various embodiments, the analysis of the time-frequency maps focuses on one or more types of waveforms in the signals that reflect cardiac activity during certain phases of the cardiac cycle, such as, for example, the T wave (which represents the repolarization of the ventricles), the QRS complex (which corresponds to the depolarization of the ventricles), and the P wave (which corresponds to atrial depolarization). Once a waveform of a particular type has been identified in the ECG and/or its associated time-frequency map, certain features of the waveform, such as one or more local extrema across one or two dimensions, may be determined in the time-frequency map, and the amplitude or position in time and/or frequency of the extrema may serve as quantitative measures. For example, in some embodiments, extrema are determined in the time-frequency map, within a time range corresponding to the waveform, across time and frequency. In other embodiments, extrema are determined across frequency only at one or more selected points in time (or substantially across frequency within one or more narrow (compared with the width of the time range corresponding to the entire waveform) time bands surrounding the selected points in time). These points (or bands) in time may be identified in the (one-dimensional) ECG, in one or more (likewise one-dimensional) sections through the time-frequency map taken at one or more particular frequencies, or in selected frequency ranges, and may correspond, e.g., to peaks of the waveforms or points preceding or following the peaks by specified amounts. The number and types of extrema generally depends on the morphology of the waveform, discriminating, for example, between monophasic and biphasic waves and/or between single-peaked and double-peaked waves, and this morphology may be determined prior to and guide the search for the extrema. Following the determination of the one or more measures quantitatively characterizing the waveform, these measures may be compared against empirical thresholds, against each other, and/or across leads to discover specific disease conditions and/or compute one or more indices indicative of heart health.

BRIEF DESCRIPTION OF THE DRAWINGS

The foregoing will more readily understood from the following description of various embodiments, in particular, when taken in conjunction with the accompanying drawings, in which:

FIGS. 3A and 3B are graphs of an example ECG for a normal heart and a scalogram resulting from its wavelet transform, respectively, in accordance with one embodiment.

FIGS. 3C and 3D are graphs of an example ECG for an abnormal heart and a scalogram resulting from its wavelet transform, respectively, in accordance with one embodiment.

FIGS. 6A-6E are example scalograms, in accordance with various embodiments, for five leads, taken for a diseased patient.

FIG. 7 is a perspective view of an example heart test device in accordance with various embodiments.

DESCRIPTION

Figure 1:
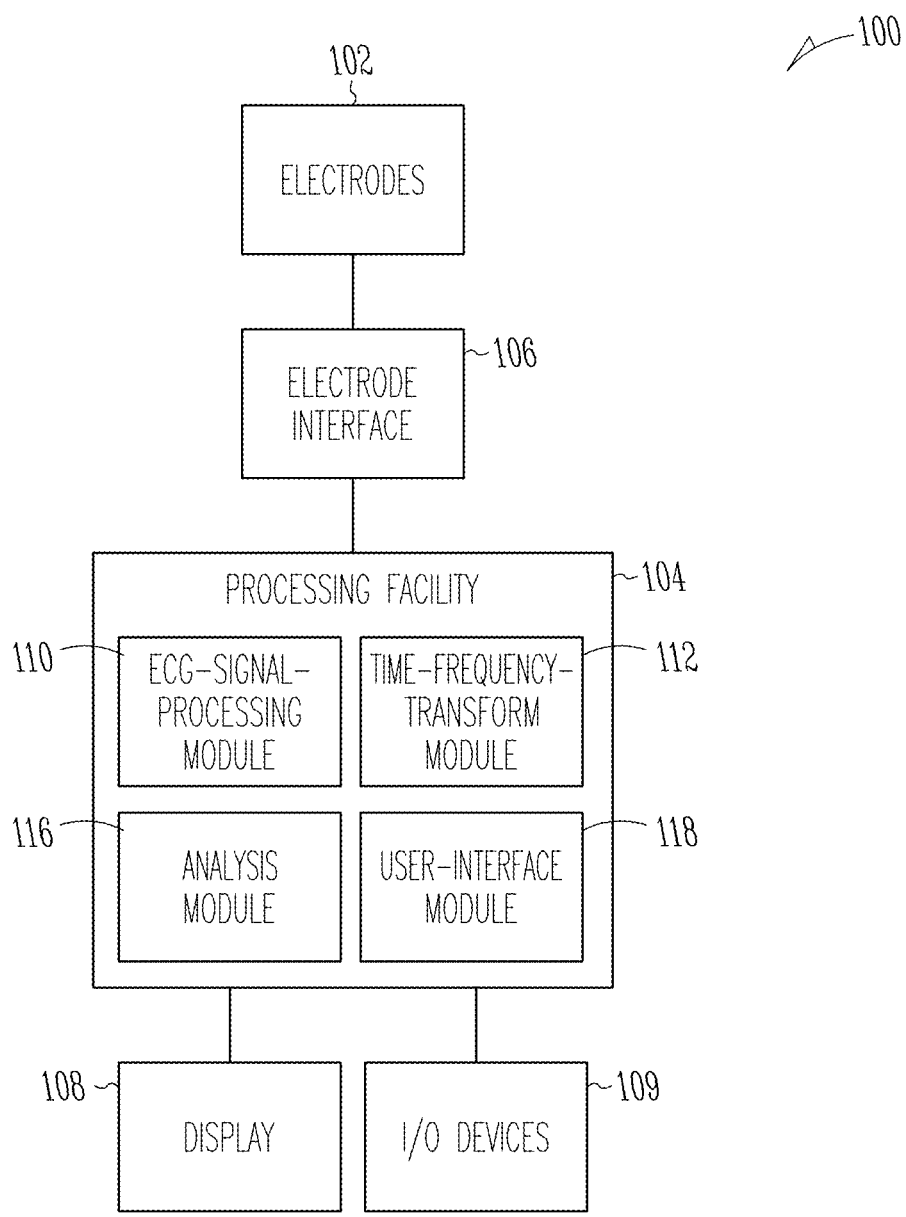
FIG. 1 is a block diagram illustrating an example system for ECG analysis in accordance with various embodiments.

FIG. 1 illustrates, in block-diagram form, various functional components of an example system for ECG analysis in accordance with various embodiments. The system 100 includes one or more electrodes 102 for acquiring ECG signals (e.g., 10 electrodes for a traditional 12-lead ECG), a processing facility 104 for processing the ECG signals, e.g., to obtain time-frequency maps and derive various measures therefrom, and an electrode interface 106 connecting the electrodes 102 to the processing facility 104. The electrode interface 106 includes circuitry that outputs electrical signals suitable as input to the processing facility 104, e.g., by digitally sampling analog input signals. The system 100 further includes a display device 108 for outputting the ECG test results (including, e.g., the ECGs, time-frequency maps, and/or various quantitative metrics and indices), and optionally other input/output devices 109, such as a keyboard and mouse and/or a printer, for instance. The display device 108 may be a touchscreen doubling as a user-input device. The processing facility 104, electrode interface 106, display 108, and input/output devices 109 may be implemented as a single, stand-alone device implementing all computational functionality for ECG signal processing and presentation. Alternatively, they may be provided by the combination of multiple communicatively coupled devices. For example, an ECG test device with limited functionality for recording and/or processing ECG signals received from one or more electrodes 102 via an electrode interface 106 of the device may outsource certain computationally intense processing tasks to other computers with which it is communicatively coupled via a wired or wireless network. Thus, the functionality of the processing facility 104 may be distributed between multiple computational devices that communicate with each other. Whether provided in a single device or distributed, the processing facility 104 may be implemented with dedicated, special-purpose circuitry (such as, e.g., a digital signal processor (DSP), field-programmable gate array (FPGA), analog circuitry, or other), a suitably programmed general-purpose computer (including at least one processor and associated memory), or a combination of both. Herein, the term "hardware processor" is used in reference to both special-purpose circuitry and general-purpose processors as used in general-purpose computers and configured via software.

The processing facility 104 may include various functionally distinct modules, such as an ECG-signal-processing module 110 that generates ECGs for multiple leads from the (e.g., digitally sampled) ECG signals for display and analysis (e.g., by filtering, smoothing, scaling, etc., as well as by combining signals for various leads as explained further below); a time-frequency transform module 112 that converts the ECG for each lead into a two-dimensional time-frequency map (signed or unsigned) and, optionally, normalizes the time-frequency map; an analysis module 116 that analyzes the ECGs and/or time-frequency maps to determine various quantitative measures and indices (which may involve, e.g., identifying delimiters between successive cardiac cycles, determining certain waveforms (such as the QRS complex, T wave, P wave) or other segments or features within the ECGs, determining quantitative measures of the waveforms from the time-frequency maps, performing various comparisons of the determined measures, computing indices indicative of heart condition and/or making qualitative diagnostic determinations, etc.), and/or a user-interface 118 module that generates graphic representations of the data provided by the other modules and assembles them into a screen for display. The ECG-signal-processing module 110 may be a conventional processing module as used in commercially available heart monitors and/or as is capable of straightforward implementation by one of ordinary skill in the art. The time-frequency transform module 112 and analysis module 116 implement algorithms and provide functionality explained in detail below, and can be readily implemented by one of ordinary skill in the art given the benefit of the present disclosure.

As will be readily appreciated, the depicted modules reflect merely one among several different possibilities for organizing the overall computational functionality of the processing facility 104. The modules may, of course, be further partitioned, combined, or altered to distribute the functionality differently. The various modules may be implemented as hardware modules, software modules executed by a general-purpose processor, or a combination of both. For example, it is conceivable to implement the time-frequency transform module 112, which generally involves the same operations for each incoming ECG signal, with special-purpose circuitry to optimize performance, while implementing the analysis module 116 in software.

While the quantification of heart function in accordance herewith is, in general, not limited to any particular number of electrodes, the system 100 includes, in various embodiments, ten electrodes 102 to facilitate obtaining a standard twelve-lead ECG, as is routinely used in the medical arts. In accordance with the standard configuration, four of the ten electrodes (conventionally labeled LA, RA, LL, RL) are placed on the patient's left and right arms and legs; two electrodes (labeled V1 and V2) are placed between the fourth and fifth ribs on the left and right side of the sternum; a further, single electrode (labeled V3) is placed between V2 and V4 on the fourth intercostal space; one electrode (labeled V4) is placed between the fifth and sixth ribs at the mid-clavicular line (the imaginary reference line that extends down from the middle of the clavicle), and, in line therewith, another electrode (labeled V5) is positioned in the anterior axillary line (the imaginary reference line running southward from the point where the collarbone and arm meet), and the tenth electrode (labeled V6) is placed on the same horizontal line as these two, but oriented along the mid-axillary line (the imaginary reference point straight down from the patient's armpit). The electric potentials measured by electrodes V1 through V6 correspond to six of the twelve standard leads; the remaining six leads correspond to the following combinations of the signals measured with the individual electrodes: I=LA–RA; II=LL–RA; III=LL–LA; aVR=RA–½ (LA+LL); aVLLA–½ (RA+LL); and aVF=LL–½ (RA+LA).

Figure 2:
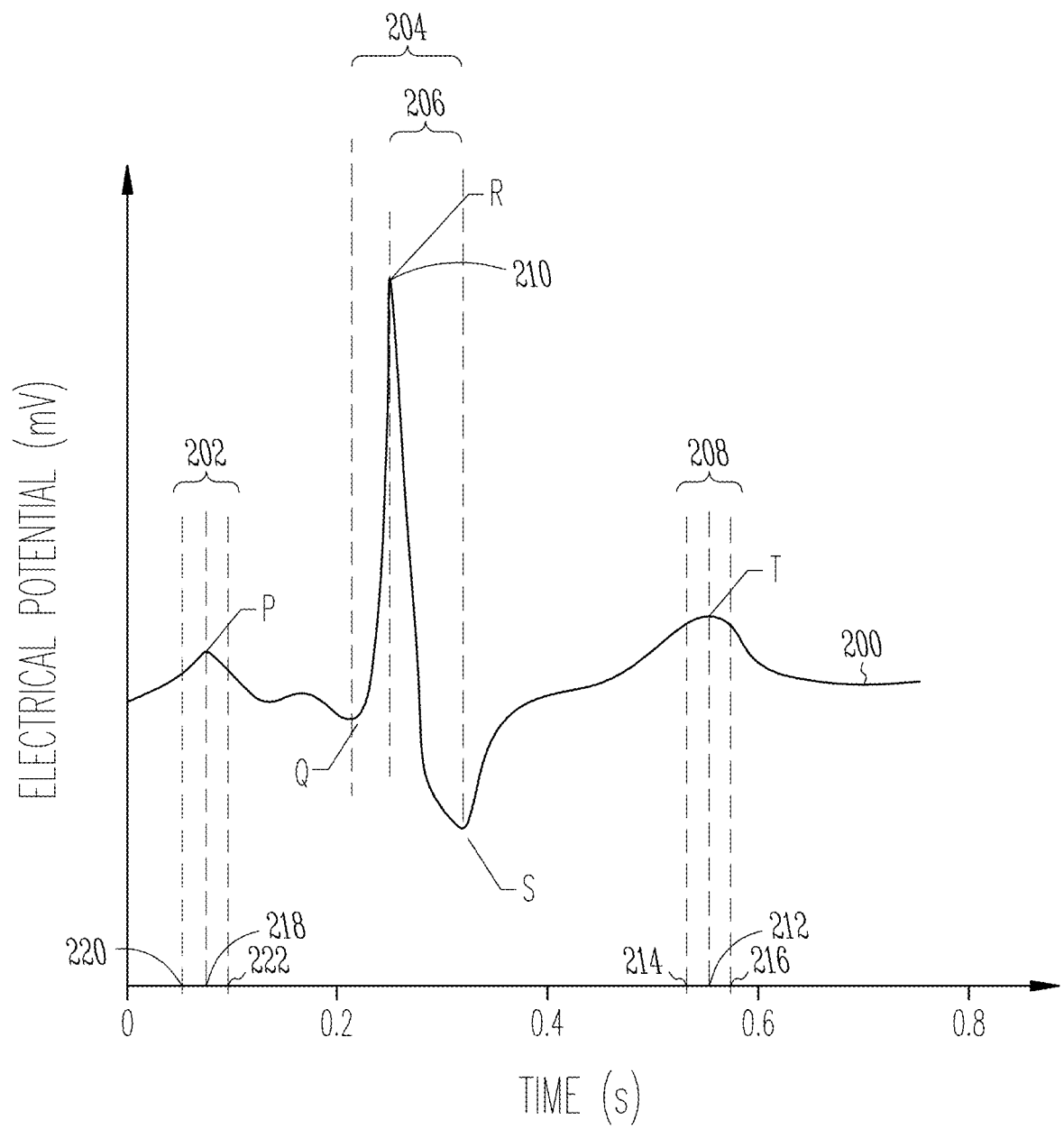
FIG. 2 is an example ECG, illustrating various waveforms and points in time used in accordance with various embodiments.

FIG. 2 schematically shows an example ECG 200 for a single cardiac cycle, illustrating the P wave 202, QRS complex 204 (which includes the RS segment 206), and T wave 208. As depicted, the electric potential usually reaches its maximum 210 at R during the QRS complex 204. However, the polarity of the signal may be inverted (such that the R peak has a negative value). Further, in some ECG signals, the S peak has a greater absolute value than the R peak. In fact, not every ECG unambiguously exhibits all the waveforms and features shown in the (rather typical) example ECG 200, or exhibits them with different waveform morphology. For example, while the depicted P wave 202 and T wave 208 each feature a single, positive peak, the waveforms may, in different ECGs (or different leads), be negative, double-peaked, or biphasic (that is, transition between positive and negative values). This uncertainty can cause difficulty in ascertaining waveforms and features, as well as in normalizing the signal based on a discrete feature of the ECG such as, e.g., the R peak. To circumvent the normalization difficulty, various embodiments base normalization not on a specific waveform feature (e.g., peak), but on a signal maximum and minimum identified across a time range, such as the time interval encompassing at least the RS segment 206 (and thus including both the R and the S peak if they are, in fact, clearly represented in the signal), irrespective of the feature to which that maximum or minimum corresponds (if any).

FIG. 2 also illustrates certain points in time at which data is evaluated in accordance with various embodiments, such as the time 212 at which the T wave 208 assumes its maximum, "early" and "late" times 214, 216 bracketing the maximum of the T wave 208, and, similarly, the time 218 at which the P wave 202 peaks and corresponding early and late times 220, 222 bracketing the maximum of the P wave 202. The early and late times 214, 216, 220, 222 may be on the rising edge and falling edge of the T wave 208 or P wave 202, respectively. In various embodiments, they are selected within ranges between the respective wave maximum and points in time preceding and following that wave maximum, respectively, at which the wave assumes some specified fraction, e.g., half, of its maximum value. For biphasic or double-peaked waveforms, relevant points in time for data evaluation may include, e.g., the respective (multiple) times at which the wave peaks in the positive or negative direction, the time(s) at which the amplitude transitions between positive and negative values, the time corresponding to the "dip" (e.g., local minimum) in a double-peaked signal, etc.

In accordance herewith, the measured ECGs are transformed into two-dimensional time-frequency maps by a suitable mathematical transform, such as, for instance, wavelet transform. For a given continuous ECG signal x(t), the continuous wavelet transform is given by:

$$W(a, b) = \frac{1}{\sqrt{a}} \int_{-\infty}^{+\infty} \overline{\psi\left(\frac{t-b}{a}\right)} x(t) dt,$$

where ψ is a selected wavelet, b corresponds to a shifted position in time and a to a scaling factor, and W(a,b) is the two-dimensional function of position in time and scale resulting from the transform, also called wavelet coefficients. Similarly, for a discretized ECG signal x(k) (where k is an integer), the continuous wavelet transform is given by:

$$W(a, b) = \frac{1}{\sqrt{a}} \sum_k x(k) \left( \int_{-\infty}^{(k+1)T} \overline{\psi\left(\frac{t-b}{a}\right)} dt - \int_{-\infty}^{kT} \overline{\psi\left(\frac{t-b}{a}\right)} dt \right),$$

where T is the sampling period. The wavelet selected for processing may be, for example, a Mexican hat wavelet, Morlet wavelet, Meyer wavelet, Shannon wavelet, Spline wavelet, or other wavelet known to those of ordinary skill in the art. Other well-known time-frequency transforms that may be used alternatively to continuous or discrete wavelet transform include, e.g., the short-term Fourier transform.

The time-frequency maps (such as, e.g., scalograms) generally include both positive and negative values, i.e., they are "signed." In some embodiments, the absolute value of the signal value (or the square of the signal value) is taken at each time-frequency point, resulting in an "unsigned" time-frequency map. Analysis of the waveforms may be based on the signed or unsigned time-frequency map or a combination of both, depending on the particular operation performed. For the purpose of displaying the time-frequency map to a user (e.g., a physician), the unsigned version may be beneficial since it avoids presenting potentially distracting information that is not of immediate, intuitively discernible clinical significance because the sign is not relevant to an intuitive interpretation of the signal value of the time-frequency map as a measure of the electrical energy of the heart.

FIGS. 3A and 3B illustrate an example ECG for a normal heart and an unsigned scalogram resulting from its wavelet transform (followed by taking the absolute value), respectively. In the scalogram, the position b corresponding to time is along the abscissa and the scale a (corresponding to frequency) along the ordinate, and the signal value W is encoded by color or, as depicted, by gray-scale. (Alternatively, W could be represented as the height in a three-dimensional surface plot shown in perspective view.) As can be seen, the various peaks of the normal ECG are reflected in relatively high intensity in the scalogram, allowing identification of the different ECG segments. For comparison, FIGS. 3C and 3D show an example ECG and associated scalogram, respectively, for an abnormal heart. Here, features that are prominent in the normal scalogram (e.g., the T wave) have rather low intensity. While this lower intensity generally tracks the lower values of the T wave in the ECG, it will be appreciated that the scalogram may provide better visual clues. Accordingly, the scalogram can aid a physician or other skilled clinician to assess heart functioning.

To facilitate meaningful comparisons between time-frequency maps derived from ECGs obtained simultaneously for different leads, the time-frequency maps may be normalized. Normalization may involve scaling and/or shifting signal values in the time-frequency map to map the range of signal values in the map (or at least a portion of the map) to a specified numerical range (hereinafter "target range"), e.g., 0 to 255 or −128 to +127 (as are convenient ranges for binary representations, and can, in turn, be straightforwardly mapped onto color or gray-scale values for display). Using a particular normalization and the associated target range consistently not only across leads, but also across measurements taken at different times and/or even for different patients may also serve to improve comparability of data over time and across the patient population, as it eliminates or at least reduces overall signal-level variations, which are often not attributable to different heart conditions, allowing physicians to focus on the clinically relevant relative signal levels within a time-frequency map.

The normalization may be based on a regional maximum and minimum defined as the maximum and minimum of the time-frequency map across frequency and across time within a selected interval, and may then be applied to a second selected interval that may or may not be the same as the first selected interval. The maximum and minimum of the time-frequency map across frequency and across time within that second selected interval are hereinafter called the absolute maximum and minimum, and they may, but need not, coincide with the regional maximum and minimum. The first selected interval is typically, but not required to be, shorter than the second selected interval. In some embodiments, the regional maximum and minimum are determined across the entire time-frequency map, corresponding to the entire measurement time of the ECG from which it is derived, and the normalization is applied over that same range (such that the first and second selected intervals are equal). In other embodiments, the regional maximum and minimum are identified within a portion of the time-frequency map that is limited in its time dimension, e.g., to an integer number of heartbeats (e.g., disregarding partial heartbeats) or only a single heartbeat. A time-frequency map encompassing multiple heartbeats may, for instance, be broken up into portions corresponding to individual heartbeats, and each portion may be normalized separately (potentially resulting in some discontinuity of the signal values in the normalized time-frequency map); in this case, first and second selected intervals are likewise equal to each other. Normalization may even be based on a time interval encompassing only part of a heartbeat, selected to likely (but not certainly) include the absolute maximum and minimum. For instance, in some embodiments, regional maximum and minimum are determined within a portion of a time-frequency map that encompasses at least the RS segment. Note, however, that it is possible for, e.g., the T wave maximum to exceed the maximum in the QRS complex. In cases where the absolute maximum and minimum of the time-frequency map lie outside the portion of the map across which the regional maximum and minimum are determined, the normalization will result in signal values exceeding the target range. (Normalization may also be applied in the time domain. In this case, the regional minimum and maximum are across time over the selected time interval.)

Normalization may be applied according to the following equation:

$$n = (d - d_{min}) * \frac{(n_{max} - n_{min})}{(d_{max} - d_{min})} + n_{min},$$

where
  n is the normalized data point;
  $n_{min}$ is the normalized target-range minimum;
  $n_{max}$ is the normalized target-range maximum;
  d is the data point to be normalized;
  $d_{min}$ is the regional minimum; and
  $d_{max}$ is the regional maximum.

For example, to map onto the target range from 0 to 255, $n_{min}$ is 0 and $n_{max}$ is 255; in effect, this normalization shifts the time-frequency map to a minimum equal to zero and thereafter scales the shifted map based on its shifted regional maximum. More generally, the normalization shifts the time-frequency map to a minimum equal to $n_{min}$ and then scales the values of the shifted time-frequency map (taken relative to the minimum value) by the ratio of the difference between maximum and minimum of the target range to the difference between the regional maximum and minimum.

Normalization can be applied to signed as well as unsigned time-frequency maps. As will be appreciated, the result of the normalization will vary depending on whether the underlying time-frequency map is signed or unsigned. For example, when mapping a signed time-frequency map with a positive R peak and a negative S peak onto the target range from 0 to 255, several of the frequencies at the point in time corresponding to the S peak will map to or near zero. However, when the normalization is applied to the absolute value of the otherwise same time-frequency map, some frequencies at points in time between R and S will now map to or near zero whereas several of the frequencies at the point in time corresponding to the S peak will map onto a relatively larger positive number within the target range.

Figure 4:
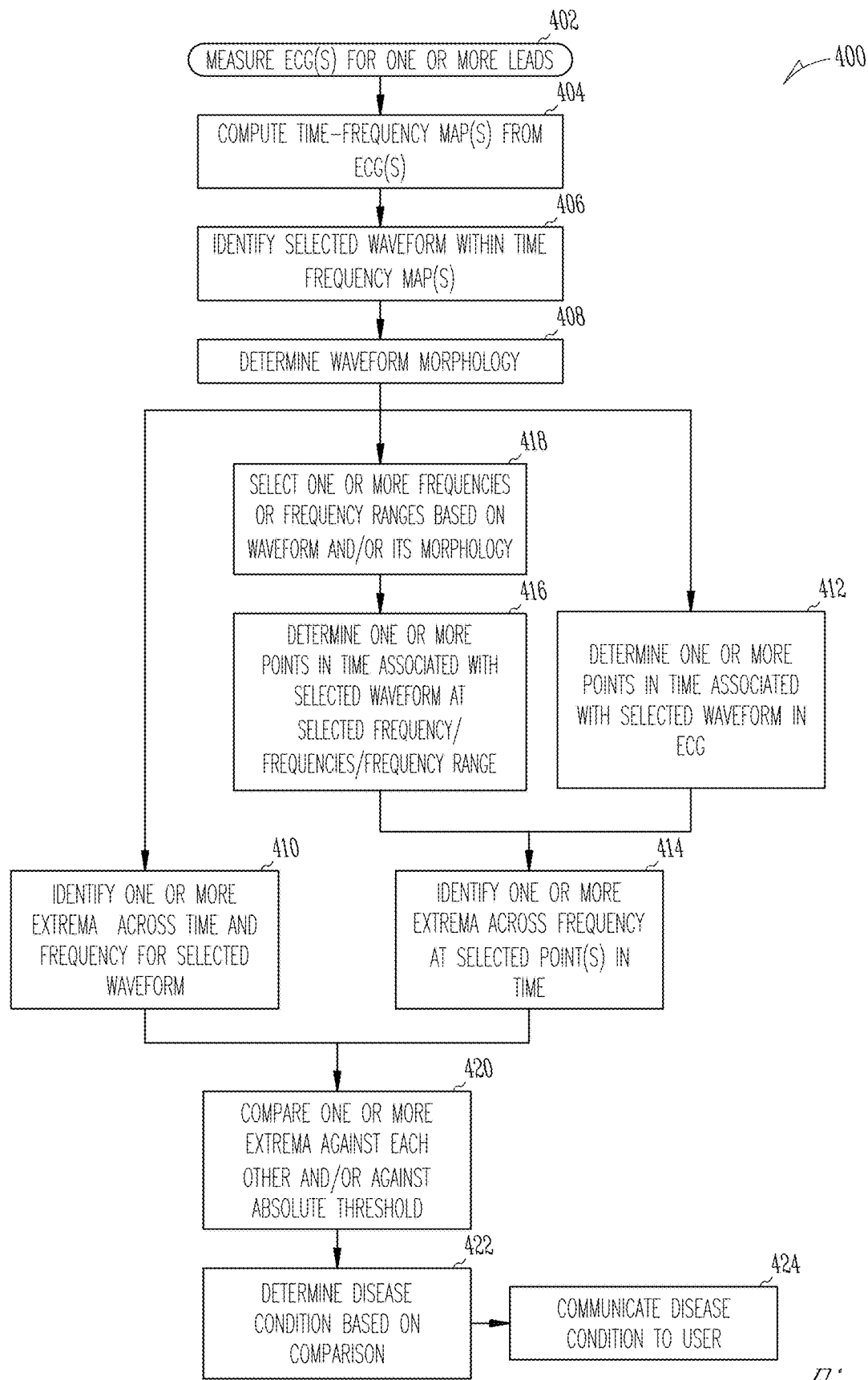
FIG. 4 is a flow chart of example methods for time-frequency analysis of ECGs in accordance with various embodiments.

FIG. 4 is a flow chart illustrating multiple variants of a method 400 for the time-frequency analysis of electrocardiograms in accordance with various embodiments. Starting point of the method 400 is the measurement of one or more ECGs associated with one or more respective leads (action 402), using one or more electrodes placed on a patient. In some embodiments, ten electrodes are used to obtain twelve leads. (The phrase "measuring electrocardiograms" is intended to encompass both the acquisition of electrocardiogram signals with the electrodes, and the digitization and/or initial processing of these signals to generate an electrocardiogram for each lead, which may include combining multiple electrocardiogram signals to obtain an electrocardiogram for a single lead, as described above.) In action 404, the ECG(s) are converted by time-frequency transform (e.g., wavelet transform) into one or more respective two-dimensional time-frequency maps (e.g., scalograms), using, e.g., the time-frequency-transform module 112 depicted in FIG. 1. The time-frequency map(s) may be used in the original signed form, or converted to unsigned map(s) by taking the absolute value at each time-frequency point, or both. Further, the time-frequency map(s) may be normalized, as described above. In some embodiments, for example, the time-frequency map is normalized based on the maximum and minimum identified in the time-frequency map across frequency and across a time interval encompassing at least the RS segment (and, in some embodiments, encompassing a full cardiac cycle (or heartbeat), multiple (an integer number of) cardiac cycles, or the entirety of the measurement time).

The time-frequency map(s) may be analyzed (wholly or partially automatically, e.g., using the analysis module 116) to characterize, qualitatively and/or quantitatively, one or more types of waveforms of interest, depending, e.g., on the specific diagnostic purpose. For example, the T wave may be analyzed to assess the health and functioning of the ventricles, and the P wave may be analyzed to assess the health and functioning of the atria. For a given type of waveform, that waveform, and the time range in which it occurs, is identified in the time-frequency map (action 406), either directly, or indirectly by first identifying the waveform in the corresponding ECG and then applying the associated time range to the analysis of the time-frequency map. In some embodiments, waveforms and features are ascertained based on their temporal relation to another feature. For example, the R peak may be used as a reference point, and high-intensity regions preceding and following the R peak by a certain amount of time (within specified margins, and generally depending on the heart rate) may then be identified as the P wave or T wave, respectively. The onset of the T wave, for instance, is known to be typically not earlier than about 120 ms after the R wave. Thus, viewing the ECG or time-frequency map in its entirety, it is usually possible to correlate the various waveforms occurring in the signals with known phases within the cardiac cycle. In embodiments that utilize ECGs and time-frequency maps for multiple leads, it may be beneficial to apply a single time range determined for a waveform consistently across data for all leads. The lead selected for determining that time range may be, e.g., the lead whose respective ECG exhibits the largest difference between the maximum and minimum value for the waveform. Alternatively, the lead with the greatest maximum-to-minimum difference for the selected waveform may serve to determine the point in time at which the waveform peaks for that lead, and that point in time may then be used as a starting point to locate the waveform and its peak in the ECGs or time-frequency maps for other leads. While these methods are amenable to straightforward automation, it is also possible, in alternative embodiments, to utilize human input in waveform identification. For example, a user interface may display the ECG and time-frequency transform in temporal alignment, and allow a user to identify waveforms, e.g., by clicking on or near waveform peaks and/or adjusting visual delimiters with a mouse or other cursor-control device.

Figure 5:
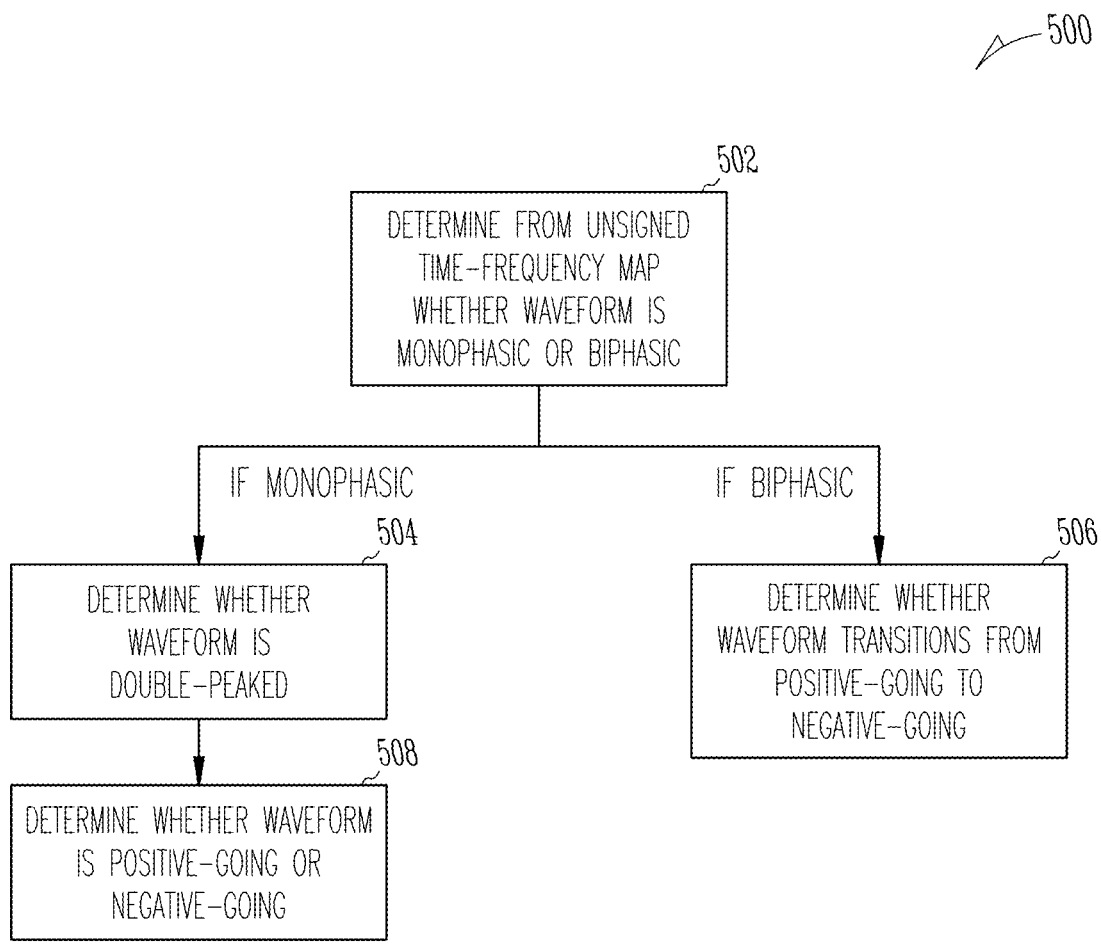
FIG. 5 is a flow chart of an example method for determining waveform morphology in accordance with various embodiments.

In various embodiments, once the time range associated with a selected waveform has been determined, the time-frequency map may be analyzed qualitatively to determine the general waveform morphology (action 408). Morphology determination may involve, for instance, distinguishing between monophasic waves (i.e., waves whose signal values are either all positive or all negative), biphasic waves (i.e., waves whose signal values transition along the wave from positive to negative or vice versa, thus forming a positive "phase" and a negative "phase" of the wave), and, optionally, triphasic waves (i.e., waves whose signal values transition twice between positive and negative, forming three "phases"). For monophasic waves, the analysis may further include determining whether the peak is positive or negative, and whether it is a single peak (i.e., a single local extremum) or double peak (i.e., a pair of local extrema separated by a small "dip"). For multiphasic waves (e.g., biphasic or triphasic waves), the analysis may include determining in which direction the signal value transitions (e.g., positive to negative or vice versa). In general, some determinations of the overall morphology can be made based on an unsigned time-frequency map whereas others may use the signed map. FIG. 5, discussed below, illustrates an example process for morphology determination. The determined morphology may inform the subsequent quantitative waveform analysis. In the absence of this optional step, the waveform is treated as monophasic by default.

Quantitative measures characterizing a waveform, such as one or more local extrema of the waveform and/or their attributes (e.g., an amplitude measure or the frequency where the extremum occurs) can be defined and determined in various ways, reflected in three partially overlapping prongs in FIG. 4. The number of extrema to be identified may generally depend on the waveform morphology. For instance, for a monophasic waveform that has not been determined to be double-peaked, a single extremum is identified, whereas for a biphasic waveform, two extrema (two maxima in an unsigned time-frequency map, and a maximum and minimum in a signed time-frequency map) are determined.

In some embodiments (reflected in the left prong), a portion of the time-frequency map corresponding to the time range determined for the selected waveform (or forming a substantial sub-range thereof) is searched in both time and frequency for one or more extrema (action 410). In other embodiments (reflected in the right prong), one or more points in time are first determined in the ECG (action 412), and the time-frequency map is then analyzed at these points in time (or in narrow bands surrounding these points in time) to determine one or more extrema across frequency only (or substantially across frequency in the case of narrow time bands) (action 414). For example, early and late times bracketing the peak of a wave may be identified in the ECG (e.g., based on a set amplitude as a fraction of peak amplitude, or based on a set time interval relative to the peak time) to determine early and late measures corresponding to the extrema across frequency at these points (or within these bands) in time. As another example, the time at which the waveform peaks in the ECG may be used to determine a peak measure corresponding to the extremum across frequency at the point (or within a band) in time where the waveform peaks. (Herein, the phrase "one or more points in time" is intended to include the case of time bands, which may be used instead of discrete points in time, e.g., to reduce the effect of noise and/or increase the robustness of the extrema determinations.)

In yet other embodiments (reflected in the center prong), the points in time at which the time-frequency map is to be identified are themselves determined from the time-frequency map by analyzing the map across time at a selected frequency or at multiple selected frequencies (or within narrow bands surrounding the selected frequencies), or across time and frequency within one or more selected frequency ranges (e.g., a low-frequency range, a high-frequency range, or a mid-frequency range) (action 416). The frequency/frequencies or frequency range(s) may be selected, e.g., based on the waveform itself and/or the waveform morphology (action 418). In general, since the inverse of the frequency (corresponding to the scale in a scalogram) can be taken as an estimate of the width of a waveform, higher frequencies may be used for narrower waveforms and waveform features while lower frequencies may be used for wider waveforms and waveform features.

For example, monophasic T waves are generally wider than monophasic P waves, so a lower frequency or frequency range (corresponding to higher scale) is used for monophasic T waves. The frequencies used for biphasic waves (whose two "humps" are usually each about half the width of a monophasic wave of the same type) are generally higher than the frequencies used for their monophasic counterparts. Double-peaked and triphasic waveforms typically use even higher frequencies (corresponding to narrower widths of the individual humps). In the case of a double-peaked waveform, first the general energy (e.g., as may be reflected in the maximum amplitude of the waveform in the time-frequency map), center location, and/or overall width may be determined at a relatively lower frequency, and second, the energy, location, and/or width of the two humps may be determined at a relatively higher frequency.

Various measures can be defined based on attributes of the identified extrema across time and/or frequency. Such measures include, for example, amplitude measures, such as the amplitude (i.e., signal value) of the extremum or an average or integral of the signal values over a small region encompassing the extremum (e.g., a region defined by signal values exceeding a specified fraction of the amplitude at the extremum), frequency measures associated with the extrema (which correspond to the inverse of the widths of the respective waveforms in the time domain), or time measures associated with the extrema (e.g., the interval between the locations in time of the maxima of the phases). These and/or similar measures may be compared against each other and/or against thresholds based on known correlations with normal and abnormal heart conditions (action 420) to ultimately compute indices indicative of heart condition and/or detect various specific disease conditions (action 422). The indices or disease conditions may then be communicated to a user (action 424), e.g., via display in a user interface on screen, in a printed report, or by email. Examples of various applications are provided below.

Referring now to FIG. 5, an example method 500 for determining the morphology of a waveform is illustrated. As shown, the morphology analysis may begin by determining from the unsigned time-frequency map whether a waveform is monophasic or biphasic (at 502). For a biphasic wave, the region for the waveform is separated by a band of low (zero or close-to-zero) values (generally depicted as a dark band) in two regions. Similarly, for a triphasic wave, the band would be separated into three distinct regions. By contrast, a monophasic wave appears as a single region without dark bands. If the waveform is determined to be monophasic, the unsigned time-frequency map may be further analyzed to determine whether the waveform is single-peaked or double-peaked (at 504). A double peak will be reflected in two extrema, separated by a region of lower, non-zero values. For a biphasic wave, the analysis may proceed to determining, from the signed time-frequency map, whether the phase transitions from positive to negative values or vice versa (at 506). Similarly, the sign of a monophasic wave may be determined from the signed time-frequency map (at 508). A positive phase in the time-frequency map corresponds to a positive-going waveform in the ECG, that is, the waveform peaks in the positive direction (i.e., first increases and then decreases in value), and a negative phase in the time-frequency map corresponds to a negative-going waveform in the ECG, that is, the waveform peaks in the negative direction (i.e., first decreases and then increases in value). (Note that "positive-going" and "negative-going" do not imply that all values of the waveform in the ECG are positive or negative, respectively, as the ECG may have an overall baseline that off-sets all values by a positive or negative amount, which may result, e.g., in a positive-going wave having negative values.) As will be appreciated, the determination of a waveform as monophasic or biphasic, and subsequent determinations of the signs associated with the peaks, may also be determined wholly based on the signed time-frequency map. In a color-coded map where blue represents negative values and red represents positive values (with green or yellow corresponding to the demarcation between positive and negative), for instance, all-red waves will be identified as monophasic positive, all-blue waves as monophasic negative, and waves transitioning from blue to red (or vice versa) as biphasic.

Of course, the degree to which waveform morphology is analyzed may differ between embodiments. In the absence of any morphology determination, the waveform is implicitly treated as monophasic. A basic morphology analysis may simply discriminate between monophasic and biphasic waveforms, whereas a more detailed analysis may distinguish between monophasic, biphasic, and double-peaked waveforms. An even more sophisticated analysis may provide determinations whether a waveform is monophasic (positive or negative), biphasic (positive-negative or negative-positive), double-peaked (positive or negative), or triphasic (positive-negative-positive or negative-positive-negative).

To illustrate different waveform morphologies in the time-frequency domain, FIGS. 6A-6E provide example ECGs and corresponding normalized, unsigned scalograms taken for a diseased patient for leads II, aVL, V1, V2, and V4, respectively. As can be seen by comparison across leads, a given waveform may assume different morphologies in different leads.

Figure 6B:
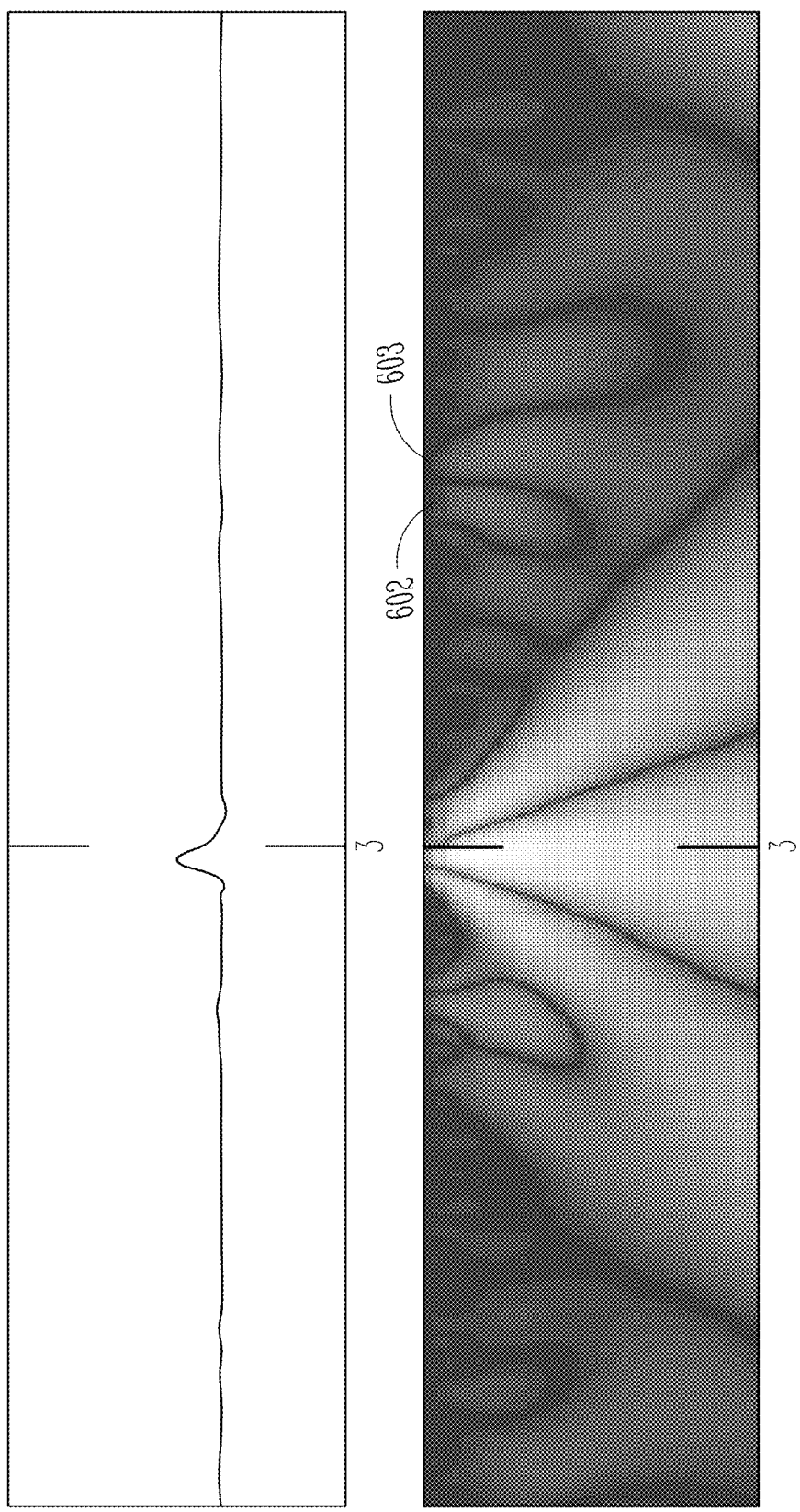

For example, with reference to FIGS. 6A and 6B, the T wave (generally indicated at 600 in the ECG of FIG. 6A, and present at the same location, but hardly visible in the ECG of FIG. 6B) is, in this example, monophasic in lead II (FIG. 6A) and biphasic in lead aVL (FIG. 6B). The monophasic wave in lead II is reflected in a bright region 601 in FIG. 6A. For lead aVL, the amplitude of the T-wave is lower, but the biphasic nature of the wave is clearly evident, in FIG. 6B, in the two lighter regions 602, 603, which correspond to the two phases within the biphasic wave. The cross-over point of the two phases is indicated by the separation between these two regions, and the location and amplitude of the two phases can be determined by the extrema in these two regions. If the type of biphasic wave (positive-negative or negative-positive) is difficult to determine from the low-level ECG amplitude, which may be off-baseline, the type can be determined from the non-normalized signed scalogram.

Figure 6C:
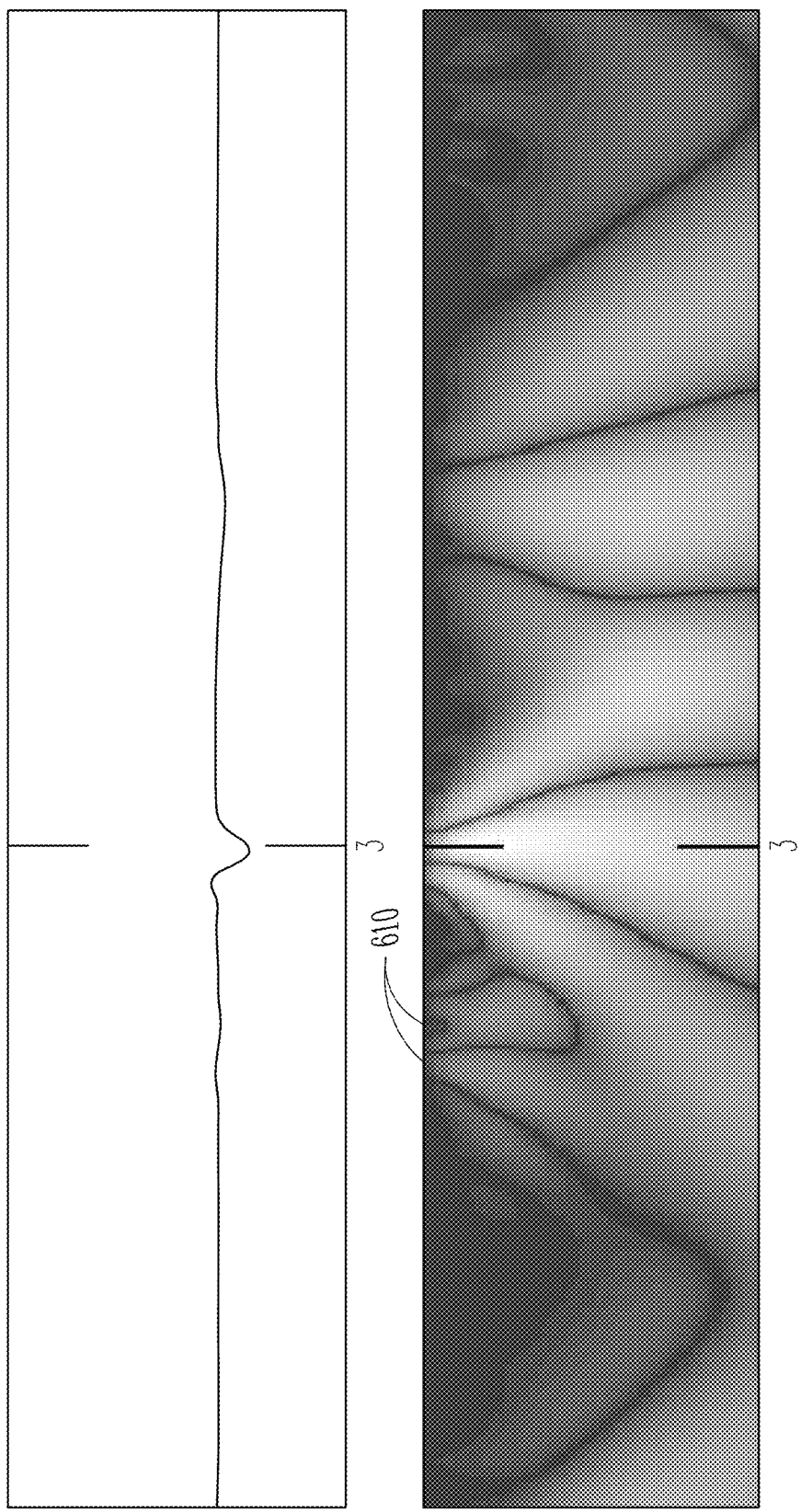
Figure 6E:
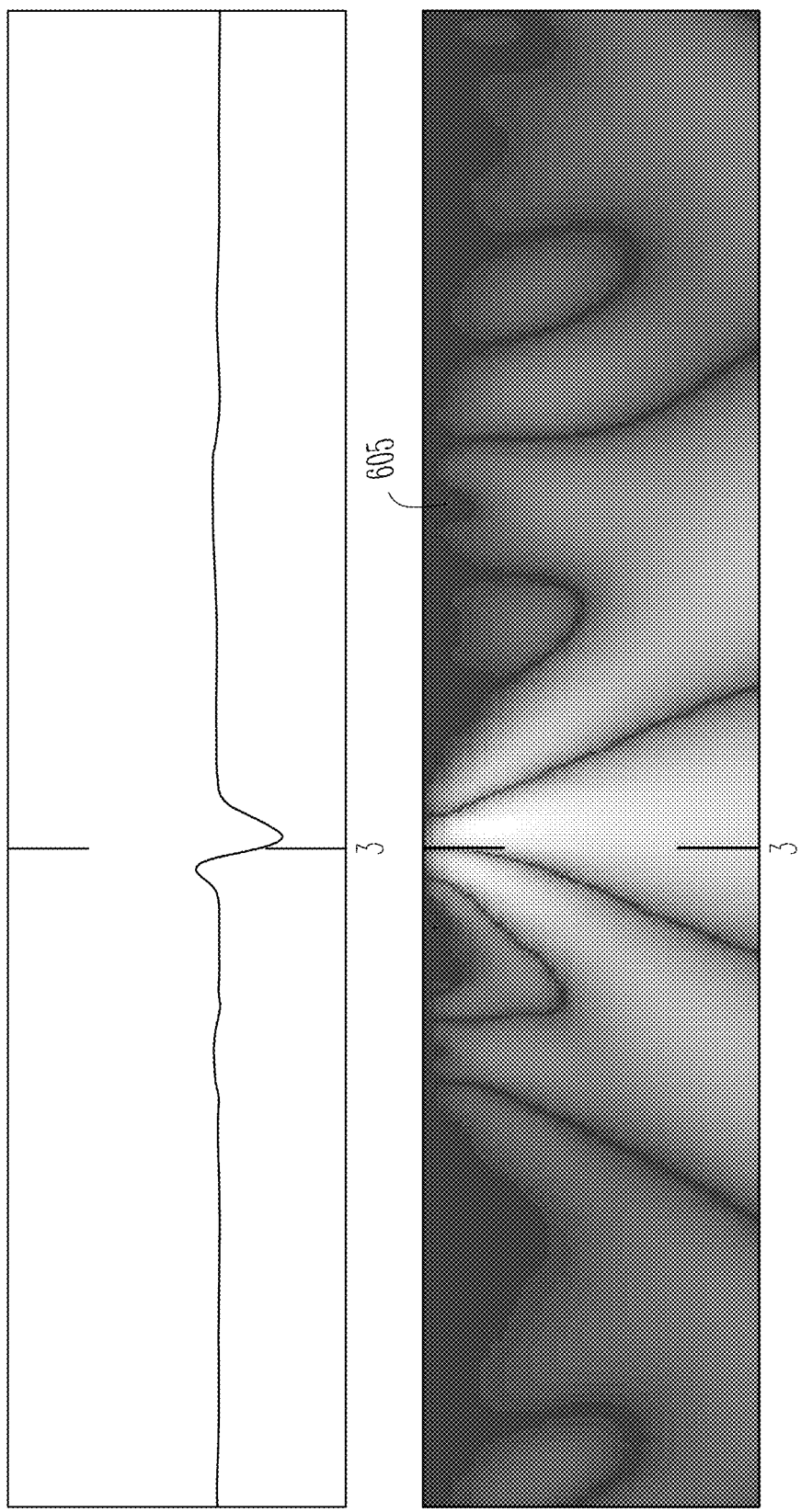

With reference to FIG. 6E, in lead V4, the T wave appears double-peaked. To find the central location of the low-level generally positive-going T-wave (which, again, is barely visible in the ECG), the gradient peak along the mid-frequencies can be used. While not always the case, the position in time for this example waveform usually corresponds to the dip 605 at the top of the scalogram frequency range, indicating the valley between the two peaks. The two (barely visible) ECG peaks of the T wave correspond to the two lighter peaks at the top of the scalogram. The position in time of these two peaks and the valley between them may serve as the points in time at which extrema across frequency are measured. While these points may be determinable from the ECG, use of the scalogram to determine these points is beneficial because the local extrema are a function of both time and frequency.

With reference to FIGS. 6A, 6C, and 6D, the P wave (indicated in the ECG of FIG. 6A at 606, and in the scalograms at 607, 608, 610) appears monophasic in V2 (FIG. 6D), biphasic in lead V1 (FIG. 6C), and double-peaked in lead II (FIG. 6A). With a double peak in lead II and a larger negative phase in V1, the patient shows signs of left atrial enlargement (discussed in more detail further below). Note that the scalogram assists in showing that the negative phase of the V1 biphasic P wave is double-peaked. By measuring the extrema at multiple points in the waveform, the measurements can be compared and a threshold can be applied to assist in determining disease state.

With reference again to FIG. 6D, showing lead V2, the local extrema (maxima) across time at a given (normalized unsigned) frequency (scale) can be used to select the Q, R, and S points in time for analysis of the QRS complex. In FIG. 6D, only the R (612) and S (614) points are shown. Note, these points in time may not be the traditionally defined locations for the Q, R, or S waveforms. Rather, these locations are designed to extract features of the waveform that correlate with disease. In turn, the extrema across the frequencies for the selected points in time can be used as the measures upon which the indices are calculated.

The above-described waveform analysis can be used to test for various specific disease conditions. For example, in one embodiment, a condition known as (right or left) atrial enlargement can be detected based on certain characteristics of the P wave. Applying the method 400 of FIG. 4 to the unsigned time-frequency map for lead V1, after having determined the P wave to be biphasic, the amplitude and frequency (being inversely proportional to temporal width) of the extrema (that is, in the unsigned time-frequency map, the maxima) of the two phases are determined. Relative to a normal biphasic P wave in V1, the maximum of the first phase (that is, the phase occurring at earlier times) being substantially larger in amplitude and being located at a substantially higher frequency (corresponding to a first phase that is shorter in time), or the maximum of the second phase (that is, the phase occurring later in time) being substantially smaller in amplitude and located at a substantially higher frequency (corresponding to a second phase that is shorter in time), can indicate right atrial enlargement (RAE). Comparing the two measured phases against each other, the first phase being substantially larger in amplitude than the second phase would likewise indicate RAE. Similarly, left atrial enlargement (LAE) can be indicated by the first maximum of the first phase being smaller in amplitude or the maximum of the second phase being larger in amplitude and at a lower frequency, relative to a normal biphasic P wave in V1, or by the first phase being substantially smaller in amplitude than the second phase. Accordingly, comparisons against absolute thresholds (e.g., statistically derived for normal condition) and/or comparisons between measurements can help determine the existence and/or the degree of RAE or LAE. A substantially larger amplitude and width of both the first and second phases may indicate the simultaneous existence of both RAE and LAE.

In the present context of comparisons between waveform extrema or other features for diagnosis of disease condition, an amplitude is deemed "substantially larger" (or "substantially smaller") than the amplitude it is compared against if it is larger (smaller) by at least a specified amount empirically determined to be (by itself or in conjunction with other conditions) abnormal, i.e., indicative of a disease condition or high likelihood of a disease condition. For example (and without limitation), the amplitude of one of the maxima of a biphasic P wave may be deemed substantially larger than the amplitude of the corresponding maximum of a normal biphasic P wave if it exceeds the latter by at least 20%, or at least 50%, or some other specified value. Similarly, a frequency associated with a maximum (or other waveform feature) is deemed "substantially lower" (or "substantially higher") than the frequency it is compared against (such as the frequency of a corresponding feature in a normal waveform) if it deviates from the latter frequency by a specified amount empirically determined to be abnormal.

When the method 400 is applied to lead II, it is first determined whether the P wave is monophasic or double-peaked. A double peak may indicate RAE and/or LAE. RAE is indicated if the first peak is substantially larger than the second peak. LAE is indicated if the second peak is substantially larger and wider than the first peak, and/or the summation of widths (as determined from the inverse of the frequencies) is substantially larger than for the normal monophasic waveform. Both RAE and LAE are indicated if the amplitudes of the phases are similar, but the second phase is substantially wider than the first and the summation of widths is substantially larger than for the normal monophasic waveform. The preceding measurements and comparisons may be fed into a set of rules to determine the likelihood of RAE and/or LAE. LAE is also an indicator of advanced diastolic dysfunction.

In another embodiment, the RS segment of the QRS complex is used to test for (right or left) ventricular hypertrophy. For this purpose, the RS segment may be treated as a biphasic waveform. Applying the method 400 to lead V1, a normal diagnosis is indicated if both phases are similar in amplitude. A substantially larger first phase indicates potential right ventricular hypertrophy (RVH), while a substantially larger second phase indicates potential left ventricular hypertrophy (LVH). In lead V6, a normal diagnosis is indicated by the first phase being about twice the amplitude of the second phase. If the second phase is twice the amplitude of the first phase, potential RVH is indicated. If the first phase is greater than four times the amplitude of the second phase, potential LVH is indicated. Similar thresholding can be applied to leads V2-V5. Suitable lead-dependent thresholds may be determined by statistical evaluation of a database of labeled patients. The measurements and comparisons may be fed into a set of rules to determine the likelihood of RVH and/or LVH.

In yet another embodiment, the T wave morphology in leads V2 and V3 is analyzed to diagnose disease. In V2 and V3, the T wave is typically positive monophasic and sometimes low-amplitude biphasic. Positive-negative biphasic T waves, known as Type 2 Wellen's syndrome, are specific for critical stenosis of the left anterior descending artery. Negative-positive biphasic T waves in leads V2-V3 can indicate hypokalaemia.

In an ECG, signal portions associated with the T wave represent the repolarization of the ventricles. The signal portions associated with the P wave, on the other hand, reflect atrial depolarization. In certain embodiments, therefore, measurements are taken at various points associated with the T wave or P wave to check for proper ventricular repolarization and atrial depolarization. For example, extrema across frequency may be determined at points in time (or within narrow time bands) where the T wave or P wave peaks (i.e., assumes its maximum) in the ECG, and/or for early and/or late points in time (or narrow time bands) preceding and/or following the maximum of the T wave or P wave and being in the vicinity of that maximum (e.g., points falling within a time interval defined by two points bracketing the T-wave or P-wave maximum at which the T wave or P wave, respectively, assumes half its maximum value). The amplitudes of the extrema (or amplitude measures corresponding to integrals or averages over the immediate neighborhood of the extrema) associated with the T wave are herein referred to as "repolarization measures" (e.g., repolarization peak, early, and late measures, respectively), and the amplitudes (or similar amplitude measures) of the extrema associated with the P wave are referred to as "depolarization measures" (e.g., depolarization peak, early, and late measures, respectively). From the repolarization and depolarization measures, one or more repolarization or depolarization indices may be derived, e.g., by averaging, dividing by the heart rate, and/or making adjustments based on information external to the ECG or time-frequency map (including, e.g., age- and/or gender-dependent adjustment factors). For example, if the repolarization/depolarization measures are obtained based on ECGs covering multiple cardiac cycles, the individually determined maxima may be averaged over these cycles. Further, the various repolarization/depolarization measures can generally be derived separately from different time-frequency maps obtained for different respective leads, and repolarization/depolarization measures of the same temporal type (e.g., the repolarization early measures) may be averaged across multiple leads. In particular, repolarization or depolarization indices specific to the left and right ventricles or atria, respectively, may be derived by averaging only across leads associated with the same (i.e., left or right) ventricle or atrium. For example, ventricular indices for the right ventricle and atrial indices for the right atrium may be calculated by (e.g., arithmetically) averaging over the repolarization measures of leads V1 and V2, and ventricular indices for the left ventricle and atrial indices for the left atrium may be calculated by averaging over the repolarization measures of leads V4, V5, and V6. In some embodiments, repolarization/depolarization measures or repolarization/depolarization indices are compared against each other, or against a threshold, to assess whether, and/or to which degree, heart function is impaired. For example, a late repolarization/depolarization measure exceeding an early repolarization/depolarization measure, a right ventricular repolarization index exceeding a left ventricular repolarization index, a right atrial depolarization index exceeding a left atrial depolarization index, or an early or late repolarization/depolarization measure falling below a specified threshold may all indicate an abnormality in heart function. An index for the heart as a whole may be computed from respective indices for the left and right ventricles or the left and right atria, e.g., by forming the ratio, difference, or some other function of left and right ventricular or atrial indices.

While some of the above examples of diagnostic applications are based on waveform morphologies that are, in principle, also detectable in time-domain ECG signals, taking measurements in the time-frequency domain, especially if the time-frequency map is a scalogram obtained by continuous wavelet transform, has multiple advantages. For instance, in a scalogram, amplitude, width (inverse-frequency), and time measurements can be made independently of determining a baseline position. In addition to minimizing the effect of residual baseline wander noise, removing the average from a generally stable recorded ECG does not ensure a zero baseline due to, for example, a large amplitude R wave and/or T wave. Measurements made by the disclosed method are not affected by any otherwise required baseline position estimation.

Further, either noise or fluctuations in the actual heart signal can mask desired information or create variability in measurements taken using the traditional time-domain ECG. The time-frequency map (and specifically the scalogram) can group energy in time and frequency to provide a measurement that is not affected by fluctuations outside the time-frequency region of interest. To further mitigate undesired signal fluctuations, the time-frequency map can be smoothed not only in time (aka filtering), but also in frequency. This is beneficial, and in some cases necessary, to facilitate the proper operation of gradient algorithms that find localized extrema across both time and frequency.

Figure 8:
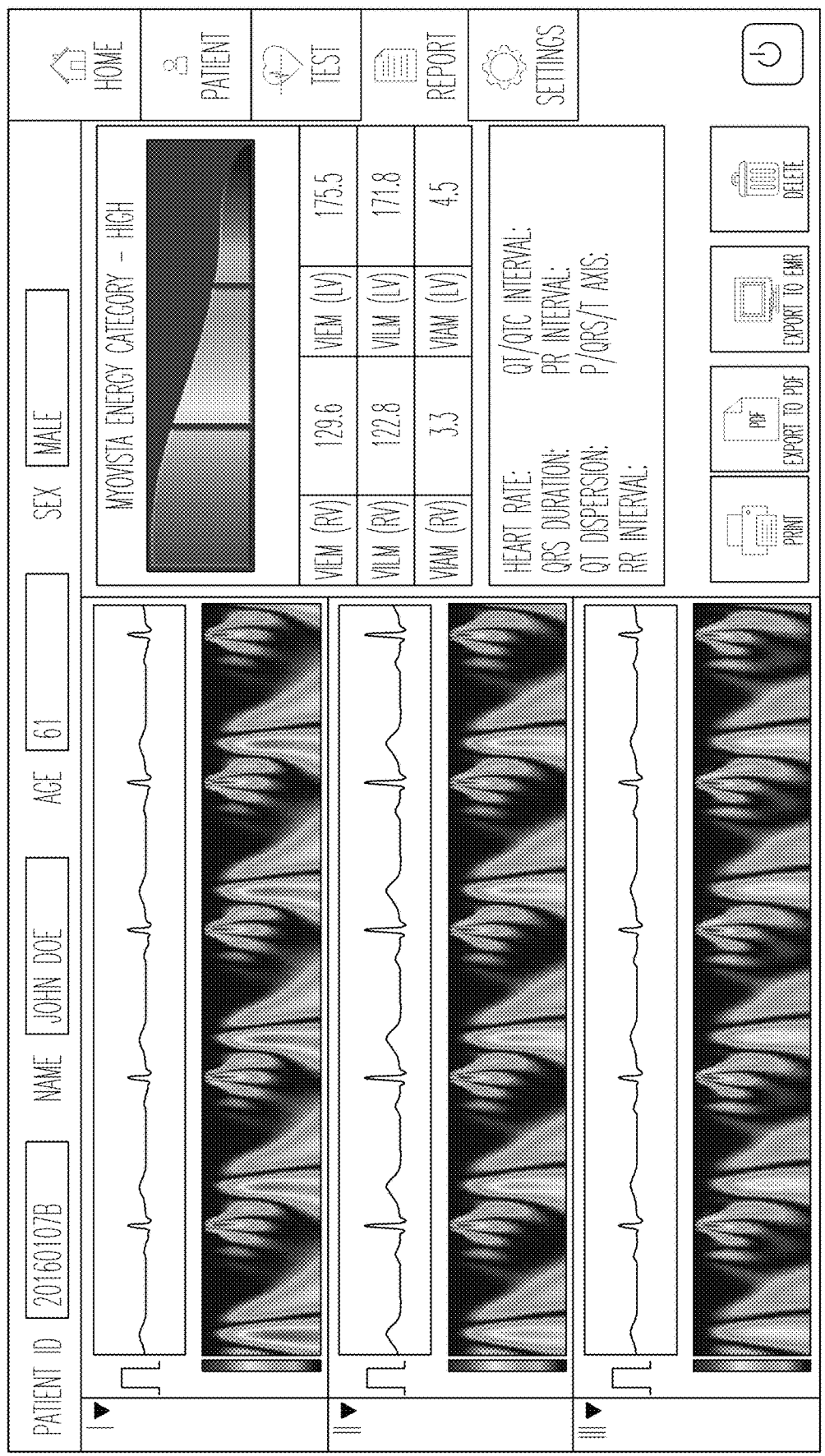
FIG. 8 is a user interface diagram showing an example report screen in accordance with various embodiments.

FIG. 7 shows an example heart test device 700 in perspective view. The depicted device takes the form of a tablet computer 700 including a touchscreen display 702 as well as a control panel 704 with physical buttons (e.g., to power the tablet 700 on/off). In some embodiments, as shown in FIG. 8, the display 702 presents a multi-tab user interface including, e.g., home, patient, test, report, and settings screens. Some of the tabs (shown along the right edge of the display 702) may be duplicated by the physical buttons of the control panel 704, allowing an operator to navigate between different screens and associated device functions in different ways. Electrodes for acquiring the ECG signals may be hooked up to the tablet computer 700 via a suitable connector 706 (e.g., a DB15 connector). The tablet 700 contains a general-purpose processor and volatile as well as non-volatile memory storing instructions for implementing the functional processing modules 110, 112, 116, 118. Of course, in various alternative embodiments, the heart test device may take different form factors, such as that of a desktop computer, laptop computer, or smartphone (to name just a few), each with a suitable electrode interface, which may include custom circuitry for converting the electrode signals into digital signals suitable for further processing with software. Furthermore, an electrocardiography system providing the functionality described herein need not necessarily be implemented in a single device, but can be provided by multiple devices used in combination, e.g., a conventional ECG monitor connected to a general-purpose computer running software to implement the processing functionality described herein.

Turning now to the user interface, FIG. 8 depicts an example report screen (as may appear within the display 702) in accordance with various embodiments. As shown, the report screen may be partitioned into multiple screen portions arranged in an intuitive manner so as to allow the viewer to quickly locate the desired information. At the top of the screen, patient information, such as a unique patient identifier and the patient's name, as well as patient-specific parameters affecting the interpretation of the ECGs, such as age and gender, may be displayed, along with a record identifier (not shown) composed of, e.g., a date and time stamp for the test. In a left panel, ECGs and time-frequency maps for one or more leads (e.g., as depicted, leads I, II, and III) may be displayed, e.g., in a vertical arrangement. The time-frequency maps can visualize information not discernible from the ECGs from which they are derived, e.g., by providing a picture of the electrical energy of the heart during various stages within the cardiac cycle, and can be useful in detecting various disease conditions, including conditions not traditionally diagnosed based on ECGs, such as, e.g., myocardial ischemia. ECGs are included in the display because of their familiarity to physicians and other medical practitioners and for the purpose of identifying temporally defined features of the signal, such as the QRS complex, P wave, and T wave. In accordance with various embodiments, the signal value of the time-frequency map (e.g., the electrical potential or voltage that is plotted as a function of time and frequency) is encoded in a color scale (reflected, in FIG. 8, in different shades of gray corresponding to the different brightness values of various colors). While the signal value itself, as resulting from the time-frequency (e.g., short-time Fourier or wavelet) transform applied to the ECG, may be a signed value (generally resulting in both positive and negative values across the map), the color-coded depicted value may be unsigned, as obtained from a signed value by computing the absolute value. Using unsigned signal values in the color-coded maps serves to represent the energy level of the time-dependent frequency content, independent of the phase of those frequencies, thus allowing the energy of either positive or negative phase to appear at the same point (along frequency) on the time-frequency map.

As described above, the ECGs and time-frequency maps may be analyzed, in accordance with various embodiments, to provide quantitative indices indicative of heart health and/or a qualitative assessment or categorization. The results of the analysis may be presented, as shown in the right panel of FIG. 7, in numerical, textual, and/or graphic form. For example, as shown, the right panel may include an "energy icon" representing the patient's overall heart health, a number of numerical indices (e.g., repolarization or depolarization indices as described above) providing a more detailed picture underneath the icon, and a conventional Glasglow-analysis textual summary underneath the numerical indices. The Glasgow-analysis summary portion may display such metrics, derived from the ECGs, as the patient's heart rate and durations of certain ECG features (such as the QRS complex). In addition, it may summarize the quality and reliability of the test, e.g., based on signal-to-noise levels of various leads. Glasgow analysis is known to those of ordinary skill in the art, and will not be further elaborated upon herein.

Certain embodiments are described herein as including a number of logic components or modules. Modules may constitute either software modules (e.g., code embodied on a non-transitory machine-readable medium or in a signal transmitted over a network) or hardware-implemented modules. A hardware-implemented module is a tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired) or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware-implemented modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice.

Figure 9:
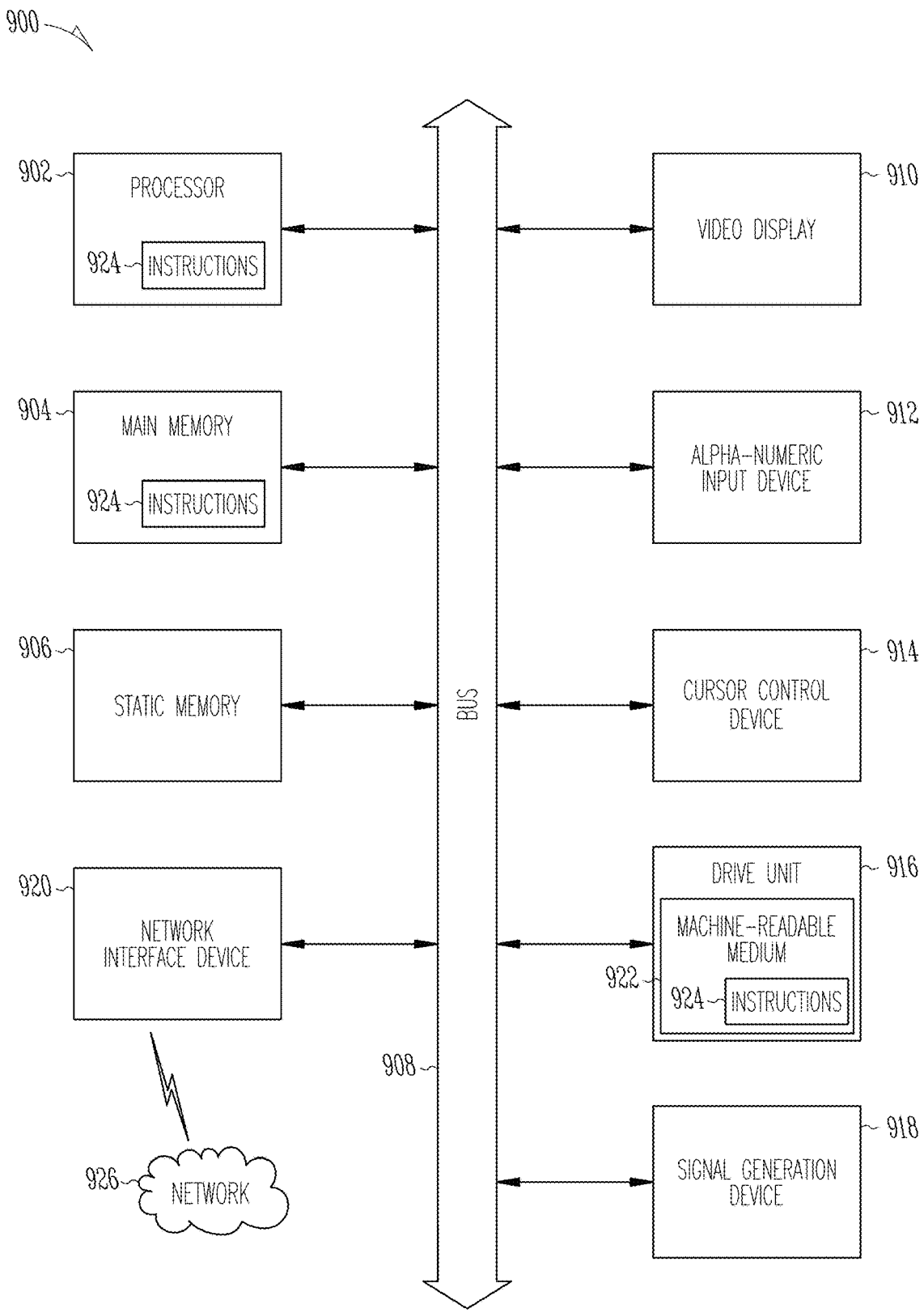
FIG. 9 is a block diagram of an example computer system as may serve as processing facility in accordance with various embodiments.

FIG. 9 is a block diagram of a machine in the example form of a computer system 900 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. While only a single machine is illustrated, the term "machine" shall also be taken to include any collection of machines that individually or jointly execute a set (or multiple sets) of instructions to perform any one or more of the methodologies discussed herein.

The example computer system 900 includes one or more processors 902 (e.g., a central processing unit (CPU), a graphics processing unit (GPU) or both), a main memory 904 and a static memory 906, which communicate with each other via a bus 908. The computer system 900 may further include a video display unit 910 (e.g., a liquid crystal display (LCD) or a cathode ray tube (CRT)). The computer system 900 also includes an alphanumeric input device 912 (e.g., a keyboard), a user interface (UI) navigation device 914 (e.g., a mouse), a disk drive unit 916, a signal generation device 918 (e.g., a speaker), a network interface device 920, and a data interface device 928 (such as, e.g., an electrode interface 106).

The disk drive unit 916 includes a machine-readable medium 922 storing one or more sets of instructions and data structures (e.g., software) 924 embodying or utilized by any one or more of the methodologies or functions described herein. The instructions 924 may also reside, completely or at least partially, within the main memory 904 and/or within the processor 902 during execution thereof by the computer system 900, the main memory 904 and the processor 902 also constituting machine-readable media.

While the machine-readable medium 922 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding, or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; CD-ROM and DVD-ROM disks, or other data-storage devices. Further, the term "machine-readable medium" shall be taken to include a non-tangible signal or transmission medium, including an electrical signal, a magnetic signal, an electromagnetic signal, an acoustic signal and an optical signal.

The following numbered examples are illustrative embodiments:

1. A method comprising, using one or more hardware processors: converting one or more electrocardiograms associated with one or more respective leads by time-frequency transform into one or more respective two-dimensional time-frequency maps; and, for a selected type of waveform, identifying the waveform of the selected type within the one or more time-frequency maps, determining one or more morphologies of the identified waveform within the one or more time-frequency maps, analyzing the one or more time-frequency maps based at least in part on the one or more morphologies of the identified waveform to determine one or more extrema associated with the identified waveform within the one or more time-frequency maps, and determining a disease condition based on at least one of one or more amplitude measures, one or more frequency measures, or one or more time measures of the determined one or more extrema.

2. The method of example 1, wherein analyzing the one or more time-frequency maps comprises analyzing at least one of the one or more time-frequency maps across time at one or more frequencies or within one or more frequency ranges selected based at least in part on a respective at least one morphology of the waveform to determine one or more points in time associated with the selected waveform, and determining the one or more extrema across frequency at the determined one or more in time.

3. The method of example 1, wherein analyzing the one or more time-frequency maps comprises determining the one or more extrema across time and frequency in the one or more time-frequency maps within a time interval associated with the waveform.

4. The method of example 1, wherein analyzing the one or more time-frequency maps comprises determining, from the respective one or more electrocardiograms, one or more points in time associated with the waveform, and determining the one or more extrema across frequency at the determined one or more points in time.

5. The method of any one of examples 1-4, wherein one or more numbers of extrema determined in the one or more time-frequency maps depend on the respective one or more morphologies of the waveform.

6. The method of any one of examples 1-5, wherein determining the disease condition comprises comparing at least one of the one or more amplitude measures, one or more frequency measures, or one or more time measures of the one or more extrema against one or more respective empirical thresholds and basing the determination of the disease condition on the comparison.

7. The method of example 6, wherein determining the disease condition comprises detecting atrial enlargement based at least in part on at least one of: comparisons of the amplitude measures and frequencies of extrema of a biphasic P wave in lead V1 against respective empirical amplitude and frequency thresholds associated with a normal biphasic P wave in lead V1; or comparison of the sum of inverse frequencies of a double-peaked monophasic P wave in lead II against an empirical threshold associated with a normal monophasic P wave in lead II.

8. The method of any one of examples 1-5, wherein the disease condition is determined based at least in part on a time-frequency map for which extrema are determined at at least two points in time, and wherein determining the disease condition comprises comparing the extrema at the at least two points in time against each other and basing the determination of the disease condition on the comparison.

9. The method of example 8, wherein determining the disease condition comprises detecting atrial enlargement based at least in part on at least one of: comparisons of amplitude measures between extrema of a biphasic P wave in lead V1; or comparisons of amplitude measures between extrema of a double-peaked monophasic P wave in lead II.

10. The method of example 8, wherein determining the disease condition comprises detecting ventricular hypertrophy based on lead-dependent comparisons of amplitude measures between extrema associated with a biphasic RS segment in any of leads V1, V2, V3, V4, V5, or V6.

11. The method of any one of examples 1-10, further comprising normalizing each of the one or more time-frequency maps based at least in part on a difference between a maximum and a minimum identified in the respective time-frequency map across time in an interval encompassing an RS segment and across frequency, wherein the extrema are determined from the normalized time-frequency maps.

12. The method of any one of examples 1-11, further comprising communicating the determined disease condition to a user.

13. One or more machine-readable media storing instructions for execution by one or more processors, the instructions causing the one or more processors to perform operations comprising: converting one or more electrocardiograms associated with one or more respective leads by time-frequency transform into one or more respective two-dimensional time-frequency maps; and for a selected type of waveform, identifying the waveform of the selected type within the one or more time-frequency maps, determining one or more morphologies of the identified waveform within the one or more time-frequency maps, analyzing the one or more time-frequency maps based at least in part on the one or more morphologies of the identified waveform to determine one or more extrema associated with the identified waveform within the one or more time-frequency maps, and, determining a disease condition based on at least one of one or more amplitude measures, one or more frequency measures, or one or more time measures of the determined one or more extrema.

14. The one or more machine-readable media of example 13, wherein analyzing the one or more time-frequency maps comprises analyzing at least one of the one or more time-frequency maps across time at one or more frequencies or within one or more frequency ranges selected based at least in part on a respective at least one morphology of the waveform to determine one or more points in time associated with the selected waveform, and determining the one or more extrema across frequency at the determined one or more in time.

15. The one or more machine-readable media of example 13, wherein analyzing the one or more time-frequency maps comprises determining, from the respective one or more electrocardiograms, one or more points in time associated with the waveform, and determining the one or more extrema across frequency at the determined one or more points in time.

16. The one or more machine-readable media of example 13, wherein analyzing the one or more time-frequency maps comprises determining the one or more extrema across time and frequency in the one or more time-frequency maps within a time interval associated with the waveform.

17. The one or more machine-readable media of any one of examples 13-16, wherein one or more numbers of extrema determined in the one or more time-frequency maps depend on the respective one or more morphologies of the waveform.

18. The one or more machine-readable media of any one of examples 13-17, wherein determining the disease condition comprises comparing at least one of the one or more amplitude measures, one or more frequency measures, or one or more time measures of the one or more extrema against one or more respective empirical thresholds and basing the determination of the disease condition on the comparison.

19. The one or more machine-readable media of examples 13-17, wherein the disease condition is determined based at least in part on a time-frequency map for which extrema are determined at at least two points in time, and wherein determining the disease condition comprises comparing the extrema at the at least two points in time against each other and basing the determination of the disease condition on the comparison.

20. A device comprising: an electrode interface configured to receive one or more electrocardiogram signals via one or more respective electrodes operatively connected to the electrode interface; and a processing facility communicatively coupled to the electrode interface and configured to: generate one or more electrocardiograms for one or more respective leads from the one or more electrocardiogram signals; convert the one or more electrocardiograms by time-frequency transform into one or more respective two-dimensional time-frequency maps; and, for a selected type of waveform, identify the waveform of the selected type within the one or more time-frequency maps, determine one or more morphologies of the identified waveform within the one or more time-frequency maps, analyze the one or more time-frequency maps based at least in part on the one or more morphologies of the identified waveform to determine one or more extrema associated with the identified waveform within the one or more time-frequency maps, and determine a disease condition based on at least one of one or more amplitude measures, one or more frequency measures, or one or more time measures of the determined one or more extrema.

21. The device of example 20, further comprising a display operatively displaying the determined disease condition to the user.

22. The device of example 20, wherein the processing facility is further configured to perform any of the operations of examples 2-12.

23. A method comprising, using one or more hardware processors: converting one or more electrocardiograms for one or more respective leads by time-frequency transform into one or more respective two-dimensional time-frequency maps; identifying, within the one or more electrocardiograms, one or more points in time associated with a P wave; determining, for at least one of the one or more time-frequency maps, one or more atrial depolarization measures corresponding to extrema across frequency of the respective time-frequency map at the one or more points in time associated with the P wave; and outputting at least one atrial depolarization index based on the one or more atrial depolarization measures.

24. The method of example 23, further comprising normalizing each of the one or more time-frequency maps based at least in part on a difference between a maximum and a minimum identified in the respective time-frequency map across time in an interval encompassing an RS segment and across frequency, wherein the one or more atrial depolarization measures are determined from the normalized time-frequency maps.

25. The method of example 24, wherein the time interval across which the maximum and minimum are identified in the time-frequency map encompasses at least one heartbeat.

26. The method of example 24, wherein the time interval across which the maximum and minimum are identified in the time-frequency map encompasses a measurement time of the associated electrocardiogram in its entirety.

27. The method of example 24, wherein the time interval across which the maximum and minimum are identified in the time-frequency map corresponds to an integer number of heartbeats.

28. The method of any one of examples 23-27, wherein the one or more points in time associated with the P wave fall within a time interval defined by points preceding and following a maximum of the P wave at which the P wave assumes half of its maximum value.

29. The method of any one of claims 23-27, wherein the one or more points in time associated with the P wave comprise a first point in time preceding the maximum of the P wave and a second point in time following the maximum of the P wave.

30. The method of any one of examples 23-29, further comprising comparing a first atrial depolarization measure corresponding to an extremum at the first point in time with a second atrial depolarization measure corresponding to an extremum at the second point in time.

31. The method of example 30, further comprising determining a heart condition based on the comparison.

32. The method of example 31, the operations further comprising causing the heart condition to be communicated to a user.

33. The method of example 31 or example 32, wherein an abnormal heart condition is determined based on the second atrial depolarization measure being greater than the first atrial depolarization measure.

34. The method of any one of examples 23-33, wherein the electrocardiograms and respective atrial depolarization measures include electrocardiograms and atrial depolarization measures for at least one lead associated with a left side of the patient's heart and at least one lead associated with a right side of the patient's heart, the method further comprising comparing a left side atrial depolarization index determined based on the at least one atrial depolarization measure determined for the left side with a right side atrial depolarization index determined based on the at least one atrial depolarization measure determined for the right side.

35. The method of example 34, further comprising determining a heart condition based on the comparison.

36. The method of example 35, the operations further comprising causing the heart condition to be communicated to a user.

37. The method of example 35 or example 36, wherein an abnormal heart condition is determined based on the right side atrial depolarization index being greater than the left side atrial depolarization index.

38. The method of any one of examples 23-37, wherein the left side atrial depolarization index comprises an average over multiple atrial depolarization measures, corresponding to extrema at a selected one of the points in time, determined based on electrocardiograms measured for multiple respective leads associated with the left side, and the right side atrial depolarization index is determined by averaging over multiple atrial depolarization measures, corresponding to extrema at the selected point in time, determined based on electrocardiograms measured for multiple respective leads associated with the right side.

39. The method of example 38, wherein the at least one atrial depolarization index comprises an average over two or more atrial depolarization measures.

40. The method of example 39, wherein the average is taken over two or more heart beats.

41. The method of example 38 or example 39, wherein the average is taken over two or more leads.

42. The method of any one of examples 23-41, wherein the at least one atrial depolarization index comprises an adjustment factor that is based on at least one of an age or a gender of the patient.

43. The method of any one of examples 23-42, wherein the at least one atrial depolarization index is based on the at least one atrial depolarization measure and a heart rate of the patient.

44. The method of any one of examples 23-43, wherein the time-frequency transform comprises a continuous wavelet transform and the time-frequency map comprises a scalogram.

45. The method of any one of examples 23-44, wherein the time-frequency maps are absolute-value maps.

46. The method of any one of examples 23-45, further comprising determining a heart condition based on a comparison of the at least one atrial depolarization index against a threshold.

47. The method of example 46, further comprising causing the heart condition to be communicated to a user.

48. The method of example 46, wherein an abnormal heart condition is determined based on the at least one atrial depolarization index being below the threshold.

49. The method of any one of examples 23-48, wherein the outputting comprises causing the at least one atrial depolarization index to be displayed in a user interface.

50. One or more machine-readable media storing instructions that, when executed by one or more processors, cause the one or more processors to perform the method of any one of examples 23-49.

51. A system comprising an electrode interface configured to receive one or more electrocardiogram signals via one or more respective electrodes operatively connected to the electrode interface; and a processing facility communicatively coupled to the electrode interface and configured to perform the method of any one of examples 23-49.

Although the invention has been described with reference to specific example embodiments, it will be evident that various modifications and changes may be made to these embodiments without departing from the broader scope of the invention. Accordingly, the specification and drawings are to be regarded in an illustrative rather than a restrictive sense.

The invention claimed is:

1. A method comprising:
using one or more hardware processors,
converting one or more electrocardiograms associated with one or more respective leads by time-frequency transform into one or more respective two-dimensional time-frequency maps; and,
for a selected electrocardiogram waveform reflecting cardiac activity during a corresponding phase of the cardiac cycle,
identifying the selected electrocardiogram waveform within the one or more time-frequency maps,
determining, from the one or more time-frequency maps, one or more waveform morphologies of the identified electrocardiogram waveform,
analyzing the one or more time-frequency maps to determine one or more extrema associated with the identified electrocardiogram waveform within the one or more time-frequency maps, the analysis being informed by the determined one or more waveform morphologies, and
determining a disease condition based on at least one of one or more amplitude measures, one or more frequency measures, or one or more time measures of the determined one or more extrema.

2. The method of claim 1, wherein analyzing the one or more time-frequency maps comprises analyzing at least one of the one or more time-frequency maps across time at one or more frequencies or within one or more frequency ranges selected based at least in part on a respective at least one waveform morphology of the electrocardiogram waveform to determine one or more points in time associated with the selected electrocardiogram waveform, and determining the one or more extrema across frequency at the determined one or more in time.

3. The method of claim 1, wherein analyzing the one or more time-frequency maps comprises determining the one or more extrema across time and frequency in the one or more time-frequency maps within a time interval associated with the electrocardiogram waveform.

4. The method of claim 1, wherein analyzing the one or more time-frequency maps comprises determining, from the respective one or more electrocardiograms, one or more points in time associated with the electrocardiogram waveform, and determining the one or more extrema across frequency at the determined one or more points in time.

5. The method of claim 1, wherein one or more numbers of extrema determined in the one or more time-frequency maps depend on the respective one or more waveform morphologies of the electrocardiogram waveform.

6. The method of claim 1, wherein determining the disease condition comprises comparing at least one of the one or more amplitude measures, one or more frequency measures, or one or more time measures of the one or more extrema against one or more respective empirical thresholds and basing the determination of the disease condition on the comparison.

7. The method of claim 6, wherein determining the disease condition comprises detecting atrial enlargement based at least in part on at least one of:
comparisons of the amplitude measures and frequencies of extrema of a biphasic P wave in lead V1 against respective empirical amplitude and frequency thresholds associated with a normal biphasic P wave in lead V1; or
comparison of the sum of inverse frequencies of a double-peaked monophasic P wave in lead II against an empirical threshold associated with a normal monophasic P wave in lead II.

8. The method of claim 1, wherein the disease condition is determined based at least in part on a time-frequency map for which extrema are determined at at least two points in time, and wherein determining the disease condition comprises comparing the extrema at the at least two points in time against each other and basing the determination of the disease condition on the comparison.

9. The method of claim 8, wherein determining the disease condition comprises detecting atrial enlargement based at least in part on at least one of:
comparisons of amplitude measures between extrema of a biphasic P wave in lead V1; or
comparisons of amplitude measures between extrema of a double-peaked monophasic P wave in lead II.

10. The method of claim 8, wherein determining the disease condition comprises detecting ventricular hypertrophy based on lead-dependent comparisons of amplitude measures between extrema associated with a biphasic RS segment in any of leads V1, V2, V3, V4, V5, or V6.

11. The method of claim 1, further comprising normalizing each of the one or more time-frequency maps based at least in part on a difference between a maximum and a minimum identified in the respective time-frequency map across time in an interval encompassing an RS segment and across frequency, wherein the extrema are determined from the normalized time-frequency maps.

12. The method of claim 1, further comprising communicating the determined disease condition to a user.

13. One or more non-transitory machine-readable media storing instructions for execution by one or more processors, the instructions causing the one or more processors to perform operations comprising:
converting one or more electrocardiograms associated with one or more respective leads by time-frequency transform into one or more respective two-dimensional time-frequency maps; and,
for a selected electrocardiogram waveform reflecting cardiac activity during a corresponding phase of a cardiac cycle,
identifying the selected electrocardiogram waveform within the one or more time-frequency maps, determining, from the one or more time-frequency maps, one or more waveform morphologies of the identified electrocardiogram waveform, analyzing the one or more time-frequency maps to determine one or more extrema associated with the identified electrocardiogram waveform within the one or more time-frequency maps, the analysis being informed by the determined one or more waveform morphologies, and determining a disease condition based on at least one of one or more amplitude measures, one or more frequency measures, or one or more time measures of the determined one or more extrema.

14. The one or more machine-readable media of claim 13, wherein analyzing the one or more time-frequency maps comprises analyzing at least one of the one or more time-frequency maps across time at one or more frequencies or within one or more frequency ranges selected based at least in part on a respective at least one waveform morphology of the electrocardiogram waveform to determine one or more points in time associated with the selected electrocardiogram waveform, and determining the one or more extrema across frequency at the determined one or more in time.

15. The one or more machine-readable media of claim 13, wherein analyzing the one or more time-frequency maps comprises determining, from the respective one or more electrocardiograms, one or more points in time associated with the electrocardiogram waveform, and determining the one or more extrema across frequency at the determined one or more points in time.

16. The one or more machine-readable media of claim 13, wherein analyzing the one or more time-frequency maps comprises determining the one or more extrema across time and frequency in the one or more time-frequency maps within a time interval associated with the waveform.

17. The one or more machine-readable media of claim 13, wherein one or more numbers of extrema determined in the one or more time-frequency maps depend on the respective one or more waveform morphologies of the electrocardiogram waveform.

18. The one or more machine-readable media of claim 13, wherein determining the disease condition comprises comparing at least one of the one or more amplitude measures, one or more frequency measures, or one or more time measures of the one or more extrema against one or more respective empirical thresholds and basing the determination of the disease condition on the comparison.

19. The one or more machine-readable media of claim 13, wherein the disease condition is determined based at least in part on a time-frequency map for which extrema are determined at at least two points in time, and wherein determining the disease condition comprises comparing the extrema at the at least two points in time against each other and basing the determination of the disease condition on the comparison.

20. A device comprising:
an electrode interface configured to receive one or more electrocardiogram signals via one or more respective electrodes operatively connected to the electrode interface; and
a processing facility communicatively coupled to the electrode interface and configured to:
generate one or more electrocardiograms for one or more respective leads from the one or more electrocardiogram signals;
convert the one or more electrocardiograms by time-frequency transform into one or more respective two-dimensional time-frequency maps; and,
for a selected electrocardiogram waveform reflecting cardiac activity during a corresponding phase of the cardiac cycle,
identify the electrocardiogram waveform of the selected type within the one or more time-frequency maps,
determine, from the one or more time-frequency maps, one or more waveform morphologies of the identified electrocardiogram waveform,
analyze the one or more time-frequency maps to determine one or more extrema associated with the identified electrocardiogram waveform within the one or more time-frequency maps, the analysis being informed by the determined one or more waveform morphologies, and
determine a disease condition based on at least one of one or more amplitude measures, one or more frequency measures, or one or more time measures of the determined one or more extrema.

21. The device of claim 20, further comprising a display operatively displaying the determined disease condition to the user.

22. The method of claim 1, wherein determining the one or more waveform morphologies comprises determining the identified waveform to be one of monophasic, biphasic, or triphasic.

23. The method of claim 1, wherein determining the one or more waveform morphologies comprises determining at least one of whether the identified waveform is single-peaked or double-peaked, whether a peak of the identified waveform is positive or negative, or whether a signal value of the identified waveform transitions from positive to negative or from negative to positive.

24. The method of claim 1, wherein the selected electrocardiogram waveform is one of a T wave, a QRS complex, or a P wave.

* * * * *